(12) United States Patent
Dartois et al.

(10) Patent No.: US 7,186,730 B2
(45) Date of Patent: Mar. 6, 2007

(54) BICYCLIC NITROGEN-CONTAINING HETEROCYCLIC DERIVATIVES FOR USE AS ANTIBACTERIALS

(75) Inventors: Catherine Genevieve Yvette Dartois, Marly-le-Roi (FR); Roger Edward Markwell, Harlow (GB); Guy Marguerite Marie Gerard Nadler, Marly-le-Roi (FR); Neil David Pearson, Harlow (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 10/477,900

(22) PCT Filed: May 24, 2002

(86) PCT No.: PCT/EP02/05709

§ 371 (c)(1),
(2), (4) Date: May 24, 2004

(87) PCT Pub. No.: WO02/096907

PCT Pub. Date: Dec. 5, 2002

(65) Prior Publication Data

US 2004/0198755 A1   Oct. 7, 2004

(30) Foreign Application Priority Data

May 25, 2001   (GB) .................................. 0112836.2

(51) Int. Cl.
*A61K 31/4375*   (2006.01)
*C07D 471/02*    (2006.01)

(52) U.S. Cl. ...................... 514/300; 546/122; 540/523; 544/105; 544/48; 544/58.2; 544/353; 514/300; 514/302; 514/230.5; 514/224.2; 514/222.5; 514/249; 514/212.07

(58) Field of Classification Search ................ 546/122, 546/115; 544/105, 58.2, 48, 353; 540/523; 514/300, 302, 230.5, 224.2, 222.5, 249, 212.07
See application file for complete search history.

(56) References Cited

U.S. PATENT DOCUMENTS

| 4,472,403 | A | * | 9/1984 | Trijzelaar et al. ............ 514/314 |
| 4,801,595 | A | | 1/1989 | Archibald et al. |
| 4,866,075 | A | | 9/1989 | Archibald et al. |
| 5,264,431 | A | | 11/1993 | Wacker et al. ............... 514/211 |
| 5,310,743 | A | | 5/1994 | Schilling et al. |
| 5,541,195 | A | | 7/1996 | Schilling et al. |
| 5,646,144 | A | | 7/1997 | Schilling et al. |
| 5,977,134 | A | | 11/1999 | Ciccarone et al. |
| 6,403,610 | B1 | | 6/2002 | Malleron et al. ............ 514/314 |
| 6,602,882 | B1 | | 8/2003 | Davies et al. ............... 514/300 |
| 6,602,884 | B2 | | 8/2003 | Bacque et al. ............... 514/314 |
| 6,603,005 | B2 | | 8/2003 | Baque et al. ................ 546/176 |
| 6,803,369 | B1 | | 10/2004 | Erskine et al. |
| 6,815,547 | B2 | | 11/2004 | Bacque et al. ............... 546/180 |
| 6,903,217 | B2 | | 6/2005 | Bacque et al. ............... 546/176 |
| 6,911,442 | B1 | | 6/2005 | Davies et al. ............. 514/230.5 |
| 6,962,917 | B2 | | 11/2005 | Davies et al. ............. 514/264.1 |
| 6,989,447 | B2 | | 1/2006 | Markwell et al. ............ 546/152 |
| 7,001,913 | B1 | | 2/2006 | Davies et al. ............... 514/300 |
| 2003/0203917 | A1 | | 10/2003 | Erskine et al. ......... 514/253.06 |
| 2003/0212084 | A1 | | 11/2003 | Hatton et al. .......... 514/266.22 |
| 2004/0053928 | A1 | | 3/2004 | Davies et al. ............... 514/248 |
| 2004/0077655 | A1 | | 4/2004 | Dartois et al. ......... 514/253.05 |
| 2004/0077656 | A1 | | 4/2004 | Markwell et al. ....... 514/253.05 |
| 2004/0138219 | A1 | | 7/2004 | Davies et al. ............... 514/243 |
| 2004/0171620 | A1 | | 9/2004 | Brooks et al. .............. 514/248 |
| 2004/0198755 | A1 | | 10/2004 | Dartois et al. ......... 514/266.22 |
| 2004/0198756 | A1 | | 10/2004 | Davies et al. .......... 514/266.22 |
| 2005/0085494 | A1 | | 4/2005 | Daines et al. .......... 514/266.22 |
| 2005/0159411 | A1 | | 7/2005 | Daines et al. ............. 514/224.8 |
| 2006/0014749 | A1 | | 1/2006 | Davies et al. ............... 514/249 |
| 2006/0079546 | A1 | | 4/2006 | Davies et al. ............... 514/300 |

FOREIGN PATENT DOCUMENTS

| CA | 2004986 | 6/1990 |
| EP | 0238868 | 9/1987 |
| EP | 0304493 | 3/1989 |
| EP | 0374095 | 6/1990 |
| EP | 0449186 | 10/1991 |
| EP | 0449187 | 10/1991 |
| EP | 0541486 | 5/1993 |
| EP | 0532456 | 3/1995 |
| EP | 0823429 | 2/1998 |
| EP | 1218370 B1 | 12/2004 |
| GB | 2184443 | 6/1987 |
| JP | 01172257 | 7/1957 |
| WO | WO95/07274 | 3/1995 |
| WO | WO95/09853 | 4/1995 |
| WO | WO96/15128 | 5/1996 |
| WO | WO97/03071 | 1/1997 |
| WO | WO97/17957 | 5/1997 |
| WO | WO97/28167 | 7/1997 |
| WO | WO97/36876 | 10/1997 |
| WO | WO97/45119 | 12/1997 |
| WO | WO98/00401 | 1/1998 |

(Continued)

OTHER PUBLICATIONS

U.S. Appl. No. 09/889820, filed Sep. 20, 2001, Davies et al.
U.S. Appl. No. 10/868351, filed Jun. 15, 2004, Erskine et al.
U.S. Appl. No. 10/199933, filed Jul. 19, 2002, Erskine et al.
U.S. Appl. No. 10/937468, filed Sep. 9, 2004, Erskine et al.

*Primary Examiner*—Zinna N. Davis
(74) *Attorney, Agent, or Firm*—Loretta J. Sauermelch; Mary E. McCarthy; Charles M. Kinzig

(57) ABSTRACT

Piperidine derivatives and pharmaceutically acceptable derivatives thereof useful in methods of treatment of bacterial infections in mammals, particularly man.

14 Claims, No Drawings

FOREIGN PATENT DOCUMENTS

| | | |
|---|---|---|
| WO | WO98/02434 | 1/1998 |
| WO | WO98/02438 | 1/1998 |
| WO | WO99/06369 | 2/1999 |
| WO | WO95/11895 | 5/1999 |
| WO | WO99/28313 | 6/1999 |
| WO | WO99/37304 | 7/1999 |
| WO | WO99/37635 | 7/1999 |
| WO | WO 00/21948 | 4/2000 |
| WO | WO0018735 | 4/2000 |
| WO | WO0021948 | 4/2000 |
| WO | WO0021952 | 4/2000 |
| WO | WO0035877 | 6/2000 |
| WO | WO 00/43383 | 7/2000 |
| WO | WO0043383 | 7/2000 |
| WO | WO0078748 | 12/2000 |
| WO | WO0102391 | 1/2001 |
| WO | WO0107432 | 2/2001 |
| WO | WO0107433 | 2/2001 |
| WO | WO0107436 | 2/2001 |
| WO | WO0114333 | 3/2001 |
| WO | WO0119788 | 3/2001 |
| WO | WO0125227 | 4/2001 |
| WO | WO0144193 | 6/2001 |
| WO | WO0153288 | 7/2001 |
| WO | WO0170673 | 9/2001 |
| WO | WO0170737 | 9/2001 |
| WO | WO0172712 | 10/2001 |
| WO | WO01/87839 | 11/2001 |
| WO | WO02/08224 | 1/2002 |
| WO | WO02/24684 | 3/2002 |
| WO | WO02/40474 | 5/2002 |
| WO | WO02/50040 | 6/2002 |
| WO | WO02/50061 | 6/2002 |
| WO | WO02/056882 | 7/2002 |
| WO | WO02/072572 | 9/2002 |
| WO | WO 02/96907 A1 | 12/2002 |
| WO | WO03/010138 | 2/2003 |
| WO | WO03/064421 | 8/2003 |
| WO | WO03/064431 | 8/2003 |
| WO | WO03/087098 | 10/2003 |

\* cited by examiner

BICYCLIC NITROGEN-CONTAINING HETEROCYCLIC DERIVATIVES FOR USE AS ANTIBACTERIALS

This invention relates to novel compounds, compositions containing them and their use as antibacterials.

WO099/37635, WO00/21948, WO0021952, WO00/43383, WO0078748, WO01/07433, WO01/07432, WO02/08224, WO02/24684 and WO01/25227 disclose piperidine and piperazine derivatives having antibacterial activity.

This invention provides a compound of formula (I) or a pharmaceutically acceptable derivative thereof:

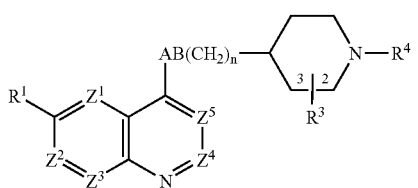

wherein:
one of $Z^1$, $Z^2$, $Z^3$, $Z^4$ and $Z^5$ is N, one is $CR^{1a}$ and the remainder are CH, or one of $Z^1$, $Z^2$, $Z^3$, $Z^4$ and $Z^5$ is $CR^{1a}$ and the remainder are CH;

$R^1$ and $R^{1a}$ are independently selected from hydrogen; hydroxy; $(C_{1-6})$ alkoxy optionally substituted by $(C_{1-6})$ alkoxy, amino, piperidyl, guanidino or amidino any of which is optionally N-substituted by one or two $(C_{1-6})$ alkyl, acyl or $(C_{1-6})$alkylsulphonyl groups, CONH2, hydroxy, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$alkoxy-substituted $(C_{1-6})$alkyl; halogen; $(C_{1-6})$alkyl; $(C_{1-6})$alkylthio; trifluoromethyl; nitro; azido; acyl; acyloxy; acylthio; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups, or when $Z^1$ is $CR^{1a}$, $R^1$ and $R^{1a}$ may together represent $(C_{1-2})$alkylenedioxy, provided that when $Z^1$, $Z^2$, $Z^3$, $Z^4$ and $Z^5$ are $CR^{1a}$ or CH, then $R^1$ is not hydrogen;

$R^3$ is hydrogen; or
$R^3$ is in the 2- or 3-position and is:

carboxy; $(C_{1-6})$alkoxycarbonyl; aminocarbonyl wherein the amino group is optionally substituted by hydroxy, $(C_{1-6})$alkyl, hydroxy$(C_{1-6})$alkyl, aminocarbonyl$(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; or $(C_{1-4})$alkyl or ethenyl optionally substituted with any of the groups listed above for $R^3$ and/or 0 to 2 groups $R^{12}$ independently selected from:

halogen; $(C_{1-6})$alkylthio; trifluoromethyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylearbonyl or $(C_{2-6})$alkenylcarbonyl; amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$alkyl, hydroxy$(C_{1-6})$alkyl, aminocarbonyl$(C_{1-6})$alkyl, $(C_{2-6})$alkenyl, $(C_{1-6})$alkoxycarbonyl, $(C_{1-6})$alkyl carbonyl, $(C_{2-6})$alkenyloxycarbonyl or $(C_{2-6})$alkenylcarbonyl and optionally further substituted by $(C_{1-6})$alkyl, hydroxy$(C_{1-6})$allyl, aminocarbonyl$(C_{1-6})$alkyl or $(C_{2-6})$alkenyl; oxo; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl; or when $R^3$ is in the 3-position it may instead be selected from hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkycarbonyl or $(C_{2-6})$alkenylcarbonyl, and amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl;

in addition when $R^3$ is disubstituted with a hydroxy or amino containing substituent and a carboxy containing substituent these may optionally together form a cyclic ester or amide linkage, respectively;

$R^{10}$ is selected from $(C_{1-4})$alkyl; $(C_{2-4})$alkenyl and aryl any of which may be optionally substituted by a group $R^{12}$ as defined above; carboxy, aminocarbonyl wherein the amino group is optionally substituted by hydroxy, $(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl or $(C_{2-6})$alkenyl; $(C_{1-6})$alkylsulphonyl; trifluoromethylsulphonyl; $(C_{2-6})$alkenylsulphonyl; $(C_{1-6})$alkoxycarbonyl; $(C_{1-6})$alkylcarbonyl; $(C_{2-6})$alkenyloxycarbonyl; and $(C_{2-6})$alkenylcarbonyl;

$R^4$ is a group —U—V—$R^5$ where $R^5$ is an optionally substituted bicyclic carbocyclic or heterocyclic ring system (A):

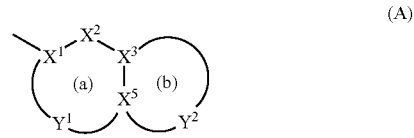

containing up to four heteroatoms in each ring in which at least one of rings (a) and (b) is aromatic;
$X^1$ is C or N when part of an aromatic ring or $CR^{14}$ or N when part of a non aromatic ring;

$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;

$X^3$ and $X^5$ are independently N or C;

$Y^1$ is a 0 to 4 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring, $Y^2$ is a 2 to 6 atom linker group, each atom of $Y^2$ being independently selected from N, $NR^{13}$, O, $S(O)_x$, CO and $CR^{14}$ when part of an aromatic or non-aromatic ring or may additionally be $CR^{14}R^{15}$ when part of a non aromatic ring;

each of $R^{14}$ and $R^{15}$ is independently selected from: H; $(C_{1-4})$alkylthio; halo; carboxy$(C_{1-4})$alkyl; halo$(C_{1-4})$ alkoxy; halo$(C_{1-4})$alkyl; $(C_{1-4})$alkyl; $(C_{2-4})$alkenyl; $(C_{1-4})$ alkoxycarbonyl; formyl; $(C_{1-4})$alkylcarbonyl; $(C_{2-4})$alkenyloxycarbonyl; $(C_{2-4})$alkenylcarbonyl; $(C_{1-4})$ alkylcarbonyloxy; $(C_{1-4})$alkoxycarbonyl$(C_{1-4})$alkyl; hydroxy; hydroxy$(C_{1-4})$alkyl; mercapto$(C_{1-4})$alkyl; $(C_{1-4})$ alkoxy, nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; aryl; aryl$(C_{1-4})$ alkyl; aryl$(C_{1-4})$alkoxy;

each $R^{13}$ is independently hydrogen, trifluoromethyl; $(C_{1-4})$alkyl optionally substituted by hydroxy, carboxy, $(C_{1-6})$alkoxycarbonyl, $(C_{1-6})$alkoxy, $(C_{1-6})$alkylthio, halo or trifluoromethyl; $(C_{2-4})$alkenyl; aryl; aryl $(C_{1-4})$ alkyl; arylcarbonyl; heteroarylcarbonyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$ alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl;

each x is independently 0, 1 or 2;

U is CO, $SO_2$ or $CH_2$ and V is $CR^{17}R^{18}$ or U is CH2 and V is CO, $SO_2$ or $CR^{17}R^{18}$;

$R^{17}$ and $R^{18}$ are independently selected from hydrogen, hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$ alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; and amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$ alkenylsulphonyl or aminocarbonyl wherein the amino group is optionally substituted by $(C_{1-6})$alkyl or $(C_{2-6})$ alkenyl;

n is 0 or 1 and AB is $NR^{11}CO$, $CONR^{11}$, $CO-CR^8R^9$, $CR^6R^7-CO$, $O-CR^8R^9$, $CR^6R^7-O$, $NHR^{11}-CR^8R^9$, $CR^6R^7-NHR^{11}$, $NR^{11}SO_2$, $CR^6R^7-SO_2$ or $CR^6R^7-CR^8R^9$;

or n is 0 or 1 and AB is NH—CO—NH or NH—CO—O;

or n is 0 and AB is $CR^6R^7SO_2NR^{11}$, $CR^6R^7CONR^{11}$ or $CR^6R^7CH_2NR^{11}$;

provided that $R^6$ and $R^7$, and $R^8$ and $R^9$ are not both optionally substituted hydroxy or amino;

and wherein:

each of $R^6$, $R^7$, $R^8$ and $R^9$ is independently selected from: H; $(C_{1-6})$alkoxy; $(C_{1-6})$alkylthio; halo; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; $(C_{2-6})$ alkenylcarbonyl; hydroxy, amino or aminocarbonyl optionally substituted as for corresponding substituents in $R^3$; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl;

or $R^6$ and $R^8$ together represent a bond and $R^7$ and $R^9$ are as above defined;

and each $R^{11}$ is independently H; trifluoromethyl; $(C_{1-6})$ alkyl; $(C_{2-6})$alkenyl; $(C_{1-6})$alkoxycarbonyl; $(C_{1-6})$alkylcarbonyl; or aminocarbonyl wherein the amino group is optionally substituted by $(C_{1-6})$alkoxycarbonyl, $(C_{1-6})$ alkylcarbonyl, $(C_{2-6})$alkenyloxycarbonyl, $(C_{2-6})$alkenylcarbonyl, $(C_{1-6})$alkyl or $(C_{2-6})$alkenyl and optionally further substituted by $(C_{1-6})$alkyl or $(C_{2-6})$alkenyl;

or where one of $R^3$ and $R^6$, $R^7$, $R^8$ or $R^9$ contains a carboxy group and the other contains a hydroxy or amino group they may together form a cyclic ester or amide linkage.

The invention also provides the use of a compound of formula (I) or a pharmaceutically acceptable derivative thereof in the manufacture of a medicament for use in the treatment of bacterial infections in mammals.

The invention also provides a pharmaceutical composition, in particular for use in the treatment of bacterial infections in mammals, comprising a compound of formula (I), or a pharmaceutically acceptable derivative thereof, and a pharmaceutically acceptable carrier.

The invention further provides a method of treatment of bacterial infections in mammals, particularly in man, which method comprises the administration to a mammal in need of such treatment of an effective amount of a a compound of formula (I), or a pharmaceutically acceptable derivative thereof.

In one aspect, when (a) and (b) are both aromatic, —U—V— is not —$CH_2$—CO— or —$(CH_2)_2$—. In another aspect when —U—V— is —$CH_2$—CO— or —$(CH_2)_2$—, $R^5$ is not indolyl, quinolinyl or benzothienyl.

In a further aspect n=0, $R^1$ and $R^{1a}$ do not together represent $(C_{1-2})$alkylenedioxy, and R13 does not represent carboxy or $(C_{1-6})$alkoxycarbonyl.

Preferably $Z^5$ is CH or N, $Z^3$ is CH or CF and $Z^1$, $Z^2$ and $Z^4$ are each CH, or $Z^1$ is N, $Z^3$ is CH or CF and $Z^2$, $Z^4$ and $Z^5$ are each CH.

When $R^1$ or $R^{1a}$ is substituted alkoxy it is preferably $(C_{2-6})$alkoxy substitituted by optionally N-substituted amino, guanidino or amidino, or $(C_{1-6})$alkoxy substituted by piperidyl. Suitable examples of $R^1$ alkoxy include methoxy, trifluoromethoxy, n-propyloxy, i-butyloxy, aminoethyloxy, aminopropyloxy, aminobutyloxy, aminopentyloxy, guanidinopropyloxy, piperidin-4-ylmethyloxy, phthalnido pentyloxy or 2-aminocarbonylprop-2-oxy. Preferably $R^1$ is methoxy, amino$(C_{3-5})$alkyloxy, guanidino$(C_{3-5})$alkyloxy, piperidyl$(C_{3-5})$alkyloxy, nitro or fluoro.

Preferably $R^1$ and $R^{1a}$ are independently methoxy, amino $(C_{3-5})$alkyloxy, guanidino$(C_{3-5})$alkyloxy, piperidyl$(C_{3-5})$ alkyloxy, nitro or fluoro; more preferably methoxy, amino $(C_{3-5})$alkyloxy or guanidino$(C_{3-5})$alkyloxy. Preferably $R^{1a}$ is H or F. Most preferably $R^1$ is methoxy and $R^{1a}$ is H or when $Z^3$ is $CR^{1a}$ it may be C—F.

When $Z^5$ is $CR^{1a}$, $R^{1a}$ is preferably hydrogen, cyano, hydroxymethyl or carboxy, most preferably hydrogen.

Preferably n is 0.

Preferred examples of $R^3$ include hydrogen; optionally substituted hydroxy, $(C_{1-4})$alkyl; ethenyl; optionally substituted 1-hydroxy-$(C_{1-4})$ alkyl; optionally substituted aminocarbonyl; carboxy$(C_{1-4})$alkyl; optionally substituted aminocarbonyl$(C_{1-4})$alkyl; cyano$(C_{1-4})$alkyl; optionally substituted 2-oxo-oxazolidinyl and optionally substituted 2-oxo-oxazolidinyl($C_{1-4}$alkyl). More preferred $R^3$ groups are hydrogen; $CONH_2$; 1-hydroxyalkyl e.g. $CH_2OH$, $CH(OH)CH_2CN$; $CH_2CO_2H$; $CH_2CONH_2$; —$CONHCH_2CONH_2$; 1,2-dihydroxyalkyl e.g. $CH(OH)$ $CH_2OH$; $CH_2CN$; 2-oxo-oxazolidin-5-yl and 2-oxo-oxazolidin-5-yl($C_{1-4}$alkyl). Most preferably $R^3$ is hydrogen or hydroxy.

When $R^3$ and $R^6$, $R^7$, $R^8$ or $R^9$ together form a cyclic ester or amide linkage, it is preferred that the resulting ring is 5–7 membered. It is further preferred that the group A or B which does not form the ester or amide linkage is $CH_2$.

When A is CH(OH) the R-stereochemistry is preferred.

Preferably A is NH, $NCH_3$, $CH_2$, CHOH, $CH(NH_2)$, C(Me)(OH) or CH(Me).

Preferably B is $CH_2$ or CO.

Preferably n=0.

Most preferably:

n is 0 and either A is CHOH or $CH_2$ and B is $CH_2$ or A is NH and B is CO.

Preferably $R^{11}$ is hydrogen or ($C_{1-4}$)alkyl e.g. methyl, more preferably hydrogen.

A preferred subgroup of compounds is where $AB(CH_2)_n$ is NHCO and $Z^1$ is N.

The group —U—V— is preferably —$(CH_2)_2$—, $CH_2CH(OH)$ or $CH_2CO$.

Preferably $R^5$ is a heterocyclic ring (A) having 8–11 ring atoms including 2–4 heteroatoms of which at least one is N or $NR^{13}$.

Preferably the heterocyclic ring (A) has ring (a) aromatic selected from optionally substituted benzo and pyrido and ring (b) non-aromatic in which preferably $Y^2$ has 3–5 atoms including a heteroatom bonded to $X^5$ selected from O, S or $NR^{13}$, where $R^{13}$ is other than hydrogen, and NHCO bonded via N to $X^3$, or O bonded to $X^3$; or ring (a) is aromatic and (b) is aromatic in which preferably $Y^2$ contains 2–3 heteroatoms, one of which is S and 1–2 are N, with one N bonded to $X^3$.

Examples of rings (A) include optionally substituted:

(a) and (b) Aromatic 1H-pyrrolo[2,3-b]-pyridin-2-yl, 1H-pyrrolo[3,2-b]-pyridin-2-yl, 3H-imidazo[4,5-b]-pyrid-2-yl, 3H-quinazolin-4-one-2-yl, benzimidazol-2-yl, benzo[1,2,3]-thiadiazol-5-yl, benzo[1,2,5]thiadiazol-5-yl, benzo[1,2,5]-oxadiazol-5-yl, benzofur-2-yl, benzothiazol-2-yl, benzo[b]thiophen-2-yl, benzoxazol-2-yl, chromen-4-one-3-yl, imidazo[1,2-a]pyridin-2-yl, imidazo-[1,2-a]-pyrimidin-2-yl, indol-2-yl, indol-6-yl, isoquinolin-3-yl, [1,8]-naphthyridine-3-yl, oxazolo[4,5-b]-pyridin-2-yl, quinolin-2-yl, quinolin-3-yl, quinoxalin-2-yl, indan-2-yl, naphthalen-2-yl, 1,3-dioxo-isoindol-2yl, benzimidazol-2-yl, benzothiophen-2-yl, 1H-benzotriazol-5-yl, 1H-indol-5-yl, 3H-benzooxazol-2-one-6-yl, 3H-benzooxazol-2-thione-6-yl, 3H-benzothiazol-2-one-5-yl, 3H-quinazolinone-2-yl, 3H-quinazolin-4-one-6-yl, 4-oxo-4H-pyrido[1,2-a]pyrimidin-3-yl, benzo[1,2,3]thiadiazol-6-yl, benzo[1,2,5]thiadiazol-5-yl, benzo[1,4]oxazin-2-one-3-yl, benzothiazol-5-yl, benzothiazol-6-yl, cinnolin-3-yl, imidazo[1,2-a]pyridazin-2-yl, imidazo[1,2-b]pyridazin-2-yl, pyrazolo[1,5-a]pyrazin-2-yl, pyrazolo[1,5-a]pyridin-2-yl, pyrazolo[1,5-a]pyrimidin-6-yl, pyrazolo[5,1-c][1,2,4]triazin-3-yl, pyrido[1,2-a]pyrimidin-4-one-2-yl, pyrido[1,2-a]pyrimidin4-one-3-yl, quinazolin-2-yl, quinoxalin-6-yl, thiazolo[3,2-a]pyrimidin-5-one-7-yl, thiazolo[5,4-b]pyridin-5-yl, thieno[3,2-b]pyridin-6-yl, 3H-benzoxazon-2-one-5-yl, oxo-4H-pyrido[1,2-a]pyrimidin-2-yl, 1-oxo-1,2-dihydro-isoquinolin-3-yl, thiazolo[4,5-b]pyridin-5-yl, [1,2,3]thiadiazolo[5,4-b]pyridin-6-yl and 2H-isoquinolin-1-one-3-yl.

(a) is Non Aromatic (2S)-2,3-dhydro-1H-indol-2-yl, (2S)-2,3-dihydro-benzo[1,4]dioxine-2-yl, 3-(R,S)3,4-dihydro-2H-benzo[1,4]thiazin-3-yl, 3-(R)-(2,3-dihydro-[1,4]dioxino[2,3-b]pyridin-3-yl, 3-(S)-(2,3-dihydro-[1,4]dioxino[2,3-b]pyridin-3-yl, 2,3-dihydro-benzo[1,4]dioxan-2-yl, 3-substituted-3H-quinazolin-4-one-2-yl, 1-oxo-1,3,4,5-tetrahydrobenzo[c]azepin-2-yl.

(b) is Non Aromatic 1,1,3-Trioxo-1,2,3,4-tetrahydro-1l$^6$-benzo[1,4]tihiazin-6-yl, benzo[1,3]dioxol-5-yl, 4H-benzo[1,4]oxazin-3-one-6-yl, 2,3-dihydro-benzo[1,4]dioxin-6-yl, 2-oxo-2,3-dihydro-benzoxazol-6-yl, 4H-benzo[1,4]oxazin-3-one-6-yl (3-oxo-3,4-dihydro-2H-benzo[1,4]oxazin-6-yl), 4H-benzo[1,4]thiazin-3-one-6-yl (3-oxo-3,4-dihydro-2H-benzo[1,4]thiazin-6-yl), 4H-benzo[1,4]oxazin-3-one-7-yl, 4-oxo-2,3,4,5-tetrahydrobenzo[b][1,4]thiazepine-7-yl, 5-oxo-2,3dihydro-5H-thiazolo[3,2-a]pyrimidin-6-yl, benzo[1,3]dioxol-5-yl, 2-oxo-2,3-dihydro-1H-pyrido[2,3-b][1,4]thiazin-7-yl, 2-oxo-2,3-dihydro-1H-pyrido[3,4-b][1,4]thiazin-7-yl, 3-oxo-3,4-dihydro-2H-2-oxo-2,3-dihydro-1H-pyrido[2,3-b]thiazin-7-yl,pyrido[3,2-b][1,4]thiazin-6-yl, 2,3-dihydro-[1,4]dioxino[2,3-b]pyridin-6-yl, 2,3-dihydro-[1,4]dioxino[2,3-c]pyridin-7-yl, 2,3-dihydro-[1,4]dioxino[2,3-b]pyridin-7-yl, [1,2,3]thiadiazolo[5,4-b]pyridin-6-yl.

6,7-dihydro-[1,4]dioxino[2,3-d]pyrimidin-2-yl, 3-oxo-3,4-dihydro-2H-pyrido[3,2-b][1,4]oxazin-6-yl, 2-oxo-2,3-dihydro-1H-pyrido[3,4-b][1,4]oxazin-7-yl, 2-oxo-2,3-dihydro-1H-pyrido[2,3-b][1,4]oxazin-7-yl, 6-oxo-6,7dihydro-5H-8-thia-1,2,5-triaza-naphthalen-3-yl, 3,4-dihydro-2H-benzo[1,4]oxazin-6-yl, 3,4-dihydro-2H-benzo[1,4]oxazin-6-yl, 3-substituted-3H-benzooxazol-2-one-6-yl, 3-substituted-3H-benzooxazole-2-thione-6-yl, 3-substituted-3H-benzothiazol-2-one-6-yl, 2,3-dihydro-1H-pyrido[2,3-b][1,4]thiazin-7-yl, 3,4-dihydro-2H-benzo[1,4]thiazin-6-yl, 3,4dihydro-1H-quinolin-2-one-7-yl, 3,4-dihydro-1H-quinoxalin-2-one-7-yl, 6,7-dihydro-4H-pyrazolo[1,5-a]pyrimidin-5-one-2-yl, 5,6,7,8-tetrahydro-[1,8]naphthyridin-2-yl, 2-oxo-3,4-dihydro-1H-[1,8]naphthyridin-6-yl.

$R^{13}$ is preferably H if in ring (a) or in addition ($C_{1-4}$)alkyl such as methyl or isopropyl when in ring (b). More preferably, in ring (b) $R^{13}$ is H when $NR^{13}$ is bonded to $X^3$ and ($C_{1-4}$)alkyl when $NR^{13}$ is bonded to $X^5$.

$R^{14}$ and $R^{15}$ are preferably independently selected from hydrogen, halo, hydroxy, ($C_{1-4}$)alkyl, ($C_{1-4}$)alkoxy, trifluoromethoxy, nitro, cyano, aryl($C_{1-4}$)alkoxy and ($C_{1-4}$)alkylsulphonyl.

More preferably $R^{15}$ is hydrogen.

More preferably each $R^{14}$ is selected from hydrogen, chloro, fluoro, hydroxy, methyl, methoxy, trifluoromethoxy, benzyloxy, nitro, cyano and methylsulphonyl. Most preferably $R^{14}$ is selected from hydrogen, hydroxy, fluorine or nitro. Preferably 0–3 groups $R^{14}$ are substituents other than hydrogen.

Most preferably $R^{14}$ and $R^{15}$ are each H.

Most preferred groups $R^5$ include:

3-oxo-3,4-dihydro-2H-benzo[1,4]thiazin-6-yl (4H-benzo[1,4]thiazin-3-one-6-yl)

benzo[1,3]dioxol-5-yl 2,3-Dihydro-benzo[1,4]dioxin-6-yl 4-fluorobenzimidazol-2-yl benzo[1,2,5]thiadiazol-5-yl 3-methyl-2-oxo-2,3-dihydro-benzooxazol-6-yl 3H-benzoxazol-2-one-5-yl
quinoxalin-2-yl
[1,2,3]thiadiazolo[5,4-b]pyridin-6-yl
2,3-Dihydro-[1,4]dioxino[2,3-b]pyridin-7-yl
2,3-Dihydro-[1,4]dioxino[2,3-c]pyridin-7-yl
2-oxo-2,3-dihydro-1H-pyrido[2,3-b][1,4]thiazin-7-yl
3-oxo-3,4-dihydro-2H-benzo[1,4]oxazin-6-yl (4H-benzo[1,4]oxazin-3-one-6-yl)
3-oxo-3,4-dihydro-2H-pyrido[3,2-b][1,4]oxazin-6-yl
6-nitro-benzo[1,3]dioxol-5-yl
7-fluoro-3-oxo-3,4-dihydro-2H-benzo[1,4]oxazin-6-yl
benzo[1,2,3]thiadiazol-5-yl
4,6-difluoro-indol-2-yl,
1H-pyrrolo[2,3-b]-pyridin-2-yl,
1H-pyrrolo[3,2-b]-pyridin-2-yl,
8-hydroxy-quinolin-2-yl,
5-fluorobenzimidazol-2-yl,
benzothiophen-2-yl,
4,6-difluoro-1H-benzimidazol-2-yl,
2,2-difluoro-benzo[1,3]dioxol-5-yl,
6-chloro-benzo[1,3]dioxol-5-yl,
2,3-Dihydro-[1,4]dioxino[2,3-b]pyridin-6-yl
3,4-dihydro-2H-benzo[1,4]oxazin-6-yl
4-oxo-4H-pyrido[1,2-a]pyrimidin-2-yl
8-Hydroxy-1-oxo-1,2-dihydro-isoquinolin-3-yl
benzothiazol-5-yl
thiazolo-[5,4-b]pyridin-6-yl
3-oxo-3,4-dihydro-2H-pyrido[3,2-b][1,4]thiazin-6-yl
7-chloro-3-oxo-3,4-dihydro-2H-pyrido[3,2-b][1,4]thiazin-6-yl
7-fluoro-3-oxo-3,4-dihydro-2H-pyrido[3,2-b][1,4]thiazin-6-yl
2-oxo-2,3-dihydro-1H-pyrido[3,4-b][1,4]thiazin-7-yl especially:
4H-benzo[1,4]thiazin-3-one-6-yl (3-oxo-3,4-dihydro-2H-benzo[1,4]thiazin-6-yl)
benzo[1,3]dioxol-5-yl
2,3-Dihydro-benzol [1,4]dioxin-6-yl
4-fluorobenzimidazol-2-yl
benzo[1,2,5]thiadiazol-5-yl
quinoxalin-2-yl
2-oxo-2,3-dihydro-1H-pyrido[2,3-b][1,4]thiazin-7-yl
2,3-dihydro-[1,4]dioxino[2,3-c]pyridin-7-yl.

When used herein, the term "alkyl" includes groups having straight and branched chains, for instance, methyl, ethyl, n-propyl, iso-propyl, n-butyl, iso-butyl, sec-butyl, t-butyl, pentyl and hexyl. The term 'alkenyl' should be interpreted accordingly.

Halo or halogen includes fluoro, chloro, bromo and iodo. Haloalkyl moieties include 1–3 halogen atoms.

Unless otherwise defined, the term 'heterocyclic' as used herein includes aromatic and non-aromatic, single and fused, rings suitably containing up to four hetero-atoms in each ring selected from oxygen, nitrogen and sulphur, which rings may be unsubstituted or C-substituted by, for example, up to three groups selected from ($C_{1-4}$)alkylthio; halo; carboxy($C_{1-4}$)alkyl; halo($C_{1-4}$)alkoxy, halo($C_{1-4}$)alkyl; ($C_{1-4}$)alkyl; ($C_{2-4}$)alkenyl; ($C_{1-4}$)alkoxycarbonyl; formyl; ($C_{1-4}$)allylcarbonyl; ($C_{2-4}$)alkenyloxycarbonyl; ($C_{2-4}$)alkenylcarbonyl; ($C_{1-4}$)allylcarbonyloxy; ($C_{1-4}$)alkoxycarbonyl($C_{1-4}$)alkyl; hydroxy, hydroxy($C_{1-4}$)alkyl; mercapto($C_{1-4}$)allyl; ($C_{1-4}$)alkoxy; nitro; cyano; carboxy; amino or aminocarbonyl optionally substituted as for corresponding substituents in $R^3$; ($C_{1-4}$)alkylsulphonyl; ($C_{2-4}$)alkenylsulphonyl; or aminosulphonyl wherein the amino group is optionally substituted by ($C_{1-4}$)alkyl or ($C_{2-4}$)alkenyl; optionally substituted aryl, aryl($C_{1-4}$)alkyl or aryl($C_{1-4}$)alkoxy and oxo groups. Each heterocyclic ring suitably has from 4 to 7, preferably 5 or 6, ring atoms. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include H; trifluoromethyl; ($C_{1-4}$)alkyl optionally substituted by hydroxy, ($C_{1-6}$)alkoxy, ($C_{1-6}$)alkylthio, halo or trifluoromethyl; ($C_{2-4}$)alkenyl; aryl; aryl ($C_{1-4}$)alkyl; ($C_{1-4}$)alkoxycarbonyl; ($C_{1-4}$)allylcarbonyl; formyl; ($C_{1-6}$)alkylsulphonyl; or aminocarbonyl wherein the amino group is optionally substituted by ($C_{1-4}$)alkoxycarbonyl, ($C_{1-4}$)alkylcarbonyl, ($C_{2-4}$)alkenyloxycarbonyl, ($C_{2-4}$)alkenylcarbonyl, ($C_{1-4}$)alkyl or ($C_{2-4}$)alkenyl and optionally further substituted by ($C_{1-4}$)allyl or ($C_{2-4}$)alkenyl.

When used herein the term 'aryl', includes phenyl and naphthyl, each optionally substituted with up to five, preferably up to three, groups selected from($C_{1-4}$)alkylthio; halo; carboxy($C_{1-4}$)alkyl; halo($C_{1-4}$)alkoxy; halo($C_{1-4}$)alkyl; ($C_{1-4}$)alkyl; ($C_{2-4}$)alkenyl; ($C_{1-4}$)alkoxycarbonyl; formyl; ($C_{1-4}$)alkylcarbonyl; ($C_{2-4}$)alkenyloxycarbonyl; ($C_{2-4}$)alkenylcarbonyl; ($C_{1-4}$)alkylcarbonyloxy, ($C_{1-4}$)alkoxycarbonyl($C_{1-4}$)alkyl; hydroxy; hydroxy($C_{1-4}$)alkyl; mercapto ($C_{1-4}$)alkyl; ($C_{1-4}$)alkoxy; nitro; cyano, carboxy, amino or aminocarbonyl optionally substituted as for corresponding substituents in $R^3$; ($C_{1-4}$)alkylsulphonyl; ($C_{2-4}$)alkenylsulphonyl; or aminosulphonyl wherein the amino group is optionally substituted by ($C_{1-4}$)alkyl or ($C_{2-4}$)alkenyl; phenyl, phenyl($C_{1-4}$)alkyl or phenyl($C_{1-4}$)alkoxy.

The term 'acyl' includes ($C_{1-6}$)alkoxycarbonyl, formyl or ($C_{1-6}$) alkylcarbonyl groups.

Some of the compounds of this invention may be crystallised or recrystalised from solvents such as aqueous and organic solvents. In such cases solvates may be formed. This invention includes within its scope stoichiometric solvates including hydrates as well as compounds containing variable amounts of water that may be produced by processes such as lyophilisation.

Since the compounds of formula (I) are intended for use in pharmaceutical compositions it will readily be understood that they are each provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or pharmaceutically acceptable derivative thereof.

Pharmaceutically acceptable derivatives of the above-mentioned compounds of formula (I) include the free base form or their acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. Compounds of formula (I) having a free carboxy group may also be prepared as an in vivo hydrolysable ester. The invention extends to all such derivatives.

Examples of suitable pharmaceutically acceptable in vivo hydrolysable ester-forming groups include those forming esters which break down readily in the human body to leave the parent acid or its salt. Suitable groups of this type include those of part formulae (i), (ii), (iii), (iv) and (v):

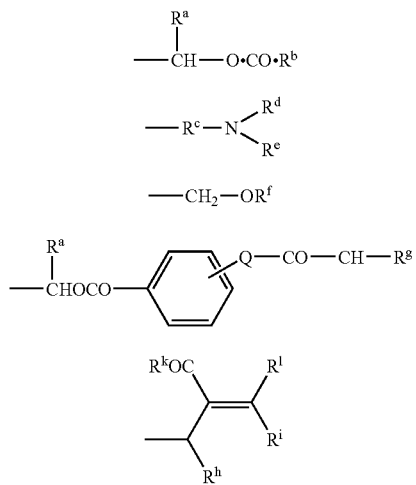

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ alkyl, or 1-$(C_{1-6}$ alkyl)amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$(C_{1-6})$alkoxy or aryl.

Examples of suitable in vivo hydrolysable ester groups include, for example, acyloxy$(C_{1-6})$alkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; $(C_{1-6})$alkoxycarbonyloxy$(C_{1-6})$alkyl groups, such as ethoxycarbonyloxymethyl, α-ethoxycarbonyloxyethyl and propoxycarbonyloxyethyl; di$(C_{1-6})$alkylamino$(C_{1-6})$alkyl especially di$(C_{1-4})$alkylamino$(C_{1-4})$alkyl groups such as dimethylaminomethyl, dimethylaminoethyl, diethylaminomethyl or diethylaminoethyl; 2-(($C_{1-6})$alkoxycarbonyl)-2-$(C_{2-6})$alkenyl groups such as 2-(isobutoxycarbonyl)pent-2-enyl and 2-(ethoxycarbonyl)but-2-enyl; lactone groups such as phthalidyl and dimethoxyphthalidyl.

A further suitable pharmaceutically acceptable in vivo hydrolysable ester-forming group is that of the formula:

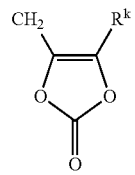

wherein $R^k$ is hydrogen, $C_{1-6}$ alkyl or phenyl.

R is preferably hydrogen.

Certain of the above-mentioned compounds of formula (I) may exist in the form of optical isomers, e.g. diastereoisomers and mixtures of isomers in all ratios, e.g. racemic mixtures. The invention includes all such forms, in particular the pure isomeric forms. For examples the invention includes compound in which an A-B group CH(OH)—CH$_2$ is in either isomeric configuration the R-isomer is preferred. The different isomeric forms may be separated or resolved one from the other by conventional methods, or any given isomer may be obtained by conventional synthetic methods or by stereospecific or asymmetric syntheses.

In a further aspect of the invention there is provided a process for preparing compounds of formula (I), or a pharmaceutically acceptable derivative thereof, which process comprises reacting a compound of formula (IV) with a compound of formula (V):

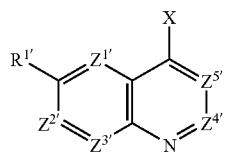

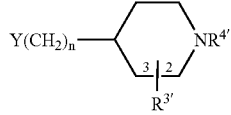

wherein n is as defined in formula (I); $Z^{1'}$, $Z^{2'}$, $Z^{3'}$, $Z^{4'}$, $Z^{5'}$, $R^{1'}$, $R^{3'}$ and $R^{4'}$ are $Z^1$, $Z^2$, $Z^3$, $Z^4$, $Z^5$, $R^1$, $R^3$ and $R^4$ as defined in formula (I) or groups convertible thereto; and X and Y may be the following combinations:

(i) one of X and Y is $CO_2R^y$ and the other is $CH_2CO_2R^x$;
(ii) X is $CHR^6R^7$ and Y is C(=O)$R^9$;
(iii) X is $CR^7$=$PR^z_3$ and Y is C(=O)$R^9$;
(iv) X is C(=O)$R^7$ and Y is $CR^9$=$PR^z_3$;
(v) one of Y and X is COW and the other is $NHR^{11'}$, NCO or NR11'COW;
(vi) X is $NHR^{11'}$ and Y is C(=O)$R^8$ or X is C(=O)$R^6$ and Y is $NHR^{11'}$;
(vii) X is $NHR^{11'}$ and Y is $CR^8R^9W$;
(viii) X is W or OH and Y is $CH_2OH$;
(ix) X is $NHR^{11'}$ and Y is $SO_2W$;
(x) one of X and Y is $(CH_2)_p$—W and the other is $(CH_2)_q NHR^{11'}$, $(CH_2)_q OH$, $(CH_2)_q SH$ or $(CH_2)_q SCOR^x$ where p+q=1;
(xi) one of X and Y is OH and the other is —CH=N$_2$;
(xii) X is NCO and Y is OH or NH$_2$;

(xiii) X is $CR^6R^7SO_2W$, A'COW, $CR^6=CH_2$ or oxirane and Y is $NHR^{11'}$;

(xiv) X is W and Y is $CONHR^{11}$ or $OCONH_2$;

in which W is a leaving group, e.g. halo, methanesulphonyloxy, trifluoromethanesulphonyloxy or imidazolyl; $R^x$ and $R^y$ are $(C_{1-6})$alkyl; $R^z$ is aryl or $(C_{1-6})$alkyl; A' and $NR^{11'}$ are A and $NR^{11}$ as defined in formula (I), or groups convertible thereto; and oxirane is:

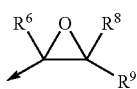

wherein $R^6$, $R^8$ and $R^9$ are as defined in formula (I);

and thereafter optionally or as necessary converting A', $Z^{1'}$, $Z^{2'}$, $Z^{3'}$, $Z^{4'}$, $Z^{5'}$, $R^{1'}$, $R^{3'}$, $R^{4'}$ and $NR^{11'}$ to A, $Z^1$, $Z^2$, $Z^3$, $Z^4$, $Z^5$, $R^1$, $R^3$, $R^4$ and $NR^{11}$; converting A-B to other A-B, interconverting $R^1$, $R^3$ and/or $R^4$, and/or forming a pharmaceutically acceptable derivative thereof.

Process variant (i) initially produces compounds of formula (I) wherein A-B is $CO—CH_2$ or $CH_2—CO$.

Process variant (ii) initially produces compounds of formula (I) wherein A-B is $CR^6R^7—CR^9OH$.

Process variant (iii) and (iv) initially produce compounds of formula (I) wherein A-B is $CR^7=CR^9$.

Process variant (v) initially produces compounds of formula (I) where A-B is $CO—NR^{11}$ or $NR^{11}—CO$.

Process variant (vi) initially produces compounds of formula (I) wherein A-B is $NR^{11}—CHR^8$ or $CHR^6—NHR^{11}$.

Process variant (vii) initially produces compounds of formula (I) wherein A-B is $NR^{11}—CR^8R^9$.

Process variant (viii) initially produces compounds of formula (I) wherein A-B is $O—CH_2$.

Process variant (ix) initially produces compounds where AB is $NR^{11}SO_2$.

Process variant (x) initially produces compounds of formula (I) wherein one of A and B is $CH_2$ and the other is $NHR^{11}$, O or S.

Process variant (xi) initially produces compounds of formula (I) wherein A-B is $OCH_2$ or $CH_2O$.

Process variant (xii) initially produces compounds where AB is NH—CO—NH or NH—CO—O.

Process variant (xiii) initially produces compounds where n is 0 and AB is $CR^6R^7SO_2NR^{11}$, A'-$CONR^{11}$ or $CR^6R^7CR^8R^9NR^{11}$.

Process variant (xiv) produces compounds where AB is $NR^{11}CO$ or NH—CO—O.

In process variants (v) and (xiii) (second variant) the reaction is a standard amide or urea formation reaction involving e.g.:

1. Activation of a carboxylic acid (e.g. to an acid chloride, mixed anhydride, active ester, O-acyl-isourea or other species), and treatment with an amine (Ogliaruso, M. A.; Wolfe, J. F. in *The Chemistry of Functional Groups* (Ed. Patai, S.) Suppl. B: *The Chemistry of Acid Derivatives, Pt.* 1 (John Wiley and Sons, 1979), pp 442–8; Beckwith, A. L. J. in *The Chemistry of Functional Groups* (Ed. Patai, S.) Suppl. B: *The Chemistry of Amides* (Ed. Zabricky, J) (John Wiley and Sons, 1970), p 73 ff. The acid and amine are preferably reacted in the presence of an activating agent such as 1-(dimethylaminopropyl)-3-ethylcarbodiimide hydrochloride (EDC) or 1-hydroxybenzotriazole (HOBT) or O-(7-azabenzotriazol-1-yl)-N,N,N',N'-tetramethyluronium hexafluorophosphate (HATU); or 2. The specific methods of:

a. in situ conversion of an acid into the amine component by a modified Curtius reaction procedure (Shioiri, T., Murata, M., Hamada, Y., *Chem. Pharm. Bull.* 1987, 35 2698)

b. in situ conversion of the acid component into the acid chloride under neutral conditions (Villeneuve, G. B.; Chan, T. H., *Tetrahedron. Lett.* 1997, 38, 6489).

A' may be, for example. protected hydroxymethylene.

The process variant (xiii) (third variant) is a standard addition reaction using methods well known to those skilled in the art. The process is preferably carried out in a polar organic solvent e.g. acetonitrile in the presence of an organic base e.g. triethylamine.

In process variant (xiii) (fourth variant) the coupling may be effected in acetonitrile at room temperature in the presence of one equivalent of lithium perchlorate as catalyst (general method of J. E. Chateauneuf et al, *J. Org. Chem.,* 56, 5939–5942, 1991) or more preferably with ytterbium triflate in dichloromethane. In some cases an levated temperature such as 40–70° C. may be beneficial. Alternatively, the piperidine ay be treated with a base, such as one equivalent of butyl lithium, and the resulting salt reacted with the oxirane in an inert solvent such as tetrahydrofuran, preferably at an elevated temperature such as 80° C. Use of a chiral epoxide will afford single diastereomers. Alternatively, mixtures of diastereomers may be separated by preparative HPLC or by conventional resolution through crystallisation of salts formed from chiral acids.

The process variant (xii) is a standard urea or carbamate formation reactions from the reaction of an isocyanate with an amine or alcohol and is conducted by methods well known to those skilled in the art (for example see March, J; *Advanced Organic Chemistry, Edition* 3 (John Wiley and Sons, 1985), p802–3). The process is preferably carried out in a polar solvent such as N,N-dimethylformamide.

In process variant (i) the process is two step: firstly a condensation using a base, preferably sodium hydride or alkoxide, sodamide, alkyl lithium or lithium dialkylamide, preferably in an aprotic solvent e.g. ether, THF or benzene; secondly, hydrolysis using an inorganic acid, preferably HCl in aqueous organic solvent at 0–100° C. Analogous routes are described in DE330945, EP31753, EP53964 and H. Sargent, J. Am. Chem. Soc. 68, 2688–2692 (1946). Similar Claisen methodology is described in Soszko et. al., Pr.Kom.Mat.Przyr.Poznan.Tow.PrzmA.Nauk., (1962), 10, 15.

In process variant (ii) the reaction is carried out in the presence of a base, preferably organometallic or metal hydride e.g. NaH, lithium diisopropylamide or NaOEt, preferably in an aprotic solvent, preferably THF, ether or benzene at −78 to 25° C. (analogous process in Gutswiller et al. (1978) J. Am. Chem. Soc. 100, 576).

In process variants (iii) and (iv) if a base is used it is preferably NaH, KH, an alkyl lithium e.g. BuLi, a metal alkoxide e.g. NaOEt, sodamide or lithium dialkylamide e.g.di-isopropylamide. An analogous method is described in U.S. Pat. No. 3,989,691 and M. Gates et. al. (1970) J. Amer.Chem.Soc., 92, 205, as well as Taylor et al. (1972) JACS 94, 6218.

In process variant (vi) the reaction is a standard reductive alkylation using, e.g., sodium borohydride or sodium triacetoxyborohydride (Gribble, G. W. in *Encyclopedia of Reagents for Organic Synthesis* (Ed. Paquette, L. A.) (John Wiley and Sons, 1995), p 4649).

The process variant (vii) is a standard alkylation reaction well known to those skilled in the art, for example where an alcohol or amine is treated with an alkyl halide in the presence of a base (for example see March, J; *Advanced Organic Chemistry*, Edition 3 (John Wiley and Sons, 1985), p364–366 and p342–343). The process is preferably carried out in a polar solvent such as N,N-dimethylformamide In process variant (xiii) (first variant) the reaction is a standard sulphonamide formation reaction well known to those skilled in the art. This may be e.g. the reaction of a sulphonyl halide with an amine.

In process variant (viii) where X is W such as halogen, methanesulphonyloxy or trifluoromethanesulphonyloxy, the hydroxy group in Y is preferably converted to an OM group where M is an alkali metal by treatment of an alcohol with a base. The base is preferably inorganic such as NaH, lithium diisopropylamide or sodium. Where X is OH, the hydroxy group in Y is activated under Mitsunobu conditions (Fletcher et.al. J Chem Soc. (1995), 623). Alternatively the X=O and Y=CH$_2$OH groups can be reacted directly by activation with 1,3-dicyclohexylcarbodiimide (DCC) (Chem. Berichte 1962, 95, 2997 or Angewante Chemie 1963 75, 377).

In process variant (ix) the reaction is conducted in the presence of an organic base such as triethylamine or pyridine such as described by Fuhrman et.al., J. Amer. Chem. Soc.; 67, 1245, 1945. The X=NR$^{11'}$SO$_2$W or Y=SO$_2$W intermediates can be formed from the requisite amine e.g. by reaction with SO$_2$Cl$_2$ analogously to the procedure described by the same authors Fuhrman et.al., J. Amer. Chem. Soc.; 67, 1245, 1945.

In process variant (x) where one of X and Y contains NHR$^{11}$ the leaving group W is halogen and the reaction is a standard amine formation reaction such as direct alkylation described in (Malpass, J. R., in *Comprehensive Organic Chemistry*, Vol. 2 (Ed. Sutherland, I. O.), p 4 ff.) or aromatic nucleophilic displacement reactions (see references cited in *Comprehensive Organic Chemistry*, Vol. 6, p 946–947 (reaction index); Smith, D. M. in *Comprehensive Organic Chemistry*, Vol. 4 (Ed. Sammes, P. G.) p 20 ff.). This is analogous to the methods described in GB 1177849.

In process variant (x) where one of X and Y contains OH or SH, this is preferably converted to an OM or SM group where M is an alkali metal by treatment of an alcohol, thiol or thioacetate with a base. The base is preferably inorganic such as NaH, lithium diisopropylamide or sodium, or, for SH, metal alkoxide such as sodium methoxide. The X/Y group containing the thioacetate SCOR$^X$ is prepared by treatment of an alcohol or alkyl halide with thioacetic acid or a salt thereof under Mitsunobu conditions. The leaving group V is a halogen. The reaction may be carried out as described in Chapman et.al., J. Chem Soc., (1956),1563, Gilligan et. al., J. Med. Chem., (1992), 35, 4344, Aloup et. al., J. Med. Chem. (1987), 30, 24, Gilnan et al., J.A.C.S. (1949), 71, 3667 and Clinton et al., J.A.C.S. (1948), 70, 491, Barluenga et al., J. Org. Chem. (1987) 52, 5190. Alternatively where X is OH and Y is CH$_2$V, V is a hydroxy group activated under Mitsunobu conditions (Fletcher et.al. J Chem Soc. (1995), 623).

In process variant (xi) the reaction is as described in den Hertzog et. al., recl.Trav. Chim. Pays-Bas, (1950),69, 700.

In process variant (xiv) the leaving group W is preferably chloro, bromo or trifluoromethylsulphonyl and the reaction is the palladium catalysed process known as the "Buchwald" reaction (J. Yin and S. L. Buchwald, Org.Lett., 2000, 2, 1101).

Reduction of a carbonyl group A or B to CHOH can be readily accomplished using reducing agents well known to those skilled in the art, e.g. sodium borohydride in aqueous ethanol or lithium alumnium hydride in ethereal solution. This is analogous to methods described in EP53964, U.S. Pat. No. 384,556 and J. Gutzwiller et al, *J. Amer. Chem. Soc.*, 1978, 100, 576.

The carbonyl group A or B may be reduced to CH$^2$ by treatment with a reducing agent such as hydrazine in ethylene glycol, at e.g. 130–160° C., in the presence of potassium hydroxide.

Reaction of a carbonyl group A or B with an organometallic reagent yields a group where R$^6$ or R$^8$ is OH and R$^7$ or R$^9$ is alkyl.

A hydroxy group on A or B may be oxidised to a carbonyl group by oxidants well known to those skilled in the art, for example, manganese dioxide, pyridinium chlorochromate or pyridinium dichromate.

A hydroxyalkyl A-B group CHR$^7$CR$^9$OH or CR$^7$(OH)CHR$^9$ may be dehydrated to give the group CR$^7$=CR$^9$ by treatment with an acid anhydride such as acetic anhydride.

Methods for conversion of CR$^7$=CR$^9$ by reduction to CHR$^7$CHR$^9$ are well known to those skilled in the art, for example using hydrogenation over palladium on carbon as catalyst. Methods for conversion of CR$^7$=CR$^9$ to give the A-B group CR$^7$(OH)CHR$^9$ or CHR$^7$CR$^9$OH are well known to those skilled in the art for example by epoxidation and subsequent reduction by metal hydrides, hydration, hydroboration or oxymercuration.

An amide carbonyl group may be reduced to the corresponding amine using a reducing agent such as lithium aluminium hydride.

A hydroxy group in A or B may be converted to azido by activation and displacement e.g. under Mitsunobu conditions using hydrazoic acid or by treatment with diphenylphosphorylazide and base, and the azido group in turn may be reduced to amino by hydrogenation.

Examples of groups Z$^{1'}$, Z$^{2'}$, Z$^{3'}$, Z$^{4'}$, Z$^{5'}$, are CR$^{1a'}$ where R$^{1a'}$ is a group convertible to R$^{1a}$, Z$^{1'}$, Z$^{2'}$, Z$^{3'}$, Z$^{4'}$ and Z$^{5'}$ are preferably Z$^1$, Z$^2$, Z$^3$, Z$^4$ and Z$^5$.

R$^{1a'}$ and R$^{1'}$ are preferably R$^{1a}$ and R$^1$. R$^{1'}$ is preferably methoxy. R$^{3'}$ is R$^3$ or more preferably hydrogen, vinyl, alkoxycarbonyl or carboxy. R$^{4'}$ is R$^4$ or more preferably H or an N-protecting group such as t-butoxycarbonyl, benzyloxycarbonyl or 9-fluorenylmethyloxycarbonyl.

Conversions of R$^{1a'}$, R$^{1'}$, R$^{3'}$ and R$^{4'}$ and interconversions of R$^{1a}$, R$^1$, R$^3$ and R$^4$ are conventional. In compounds which contain an optionally substituted hydroxy group, suitable conventional hydroxy protecting groups which may be removed without disrupting the remainder of the molecule include acyl and alkylsilyl groups. N protecting groups are removed by conventional methods.

For example R$^{1'}$ methoxy is convertible to R$^{1'}$ hydroxy by treatment with lithium and diphenylphosphine (general method described in Ireland et. al. (1973) J.Amer.Chem.Soc.,7829) or HBr. Alkylation of the hydroxy group with a suitable alkyl derivative bearing a leaving group such as halide and a protected amino, piperidyl, amidino or guanidino group or group convertible thereto, yields, after conversion/deprotection, R$^1$ alkoxy substituted by optionally N-substituted amino, piperidyl, guanidino or amidino.

R$^3$ alkenyl is convertible to hydroxyalkyl by hydroboration using a suitable reagent such as 9-borabicyclo[3.3.1] nonane, epoxidation and reduction or oxymercuration.

R$^3$ 1,2-dihydroxy can be prepared from R$^{3'}$ alkenyl using osmium tetroxide or other reagents well known to those skilled in the art (see Advanced Organic Chemistry (Ed.

March, J) (John Wiley and Sons, 1985), p 732–737 and refs. cited therein) or epoxidation followed by hydrolysis (see Advanced Organic Chemistry (Ed. March, J) (John Wiley and Sons, 1985), p 332,333 and refs. cited therein).

$R^3$ vinyl can be chain extended by standard homologation e.g by conversion to hydroxyethyl followed by oxidation to the aldehyde which is then subjected to a Wittig reaction.

Opening an epoxide $R^{3'}$ group with cyanide anion yields a CH(OH)—CH$_2$CN group.

Opening an epoxide-containing $R^{3'}$ group with azide anion yields an azide derivative which can be reduced to the amine. Conversion of the amine to a carbamate is followed by ring closure with base to give the 2-oxo-oxazolidinyl containing $R^3$ group.

Substituents on $R^3$ alkyl or alkenyl may be interconverted by conventional methods, for example hydroxy may be derivatised by esterification, acylation or etherification. Hydroxy groups may be converted to halogen, thiol, alkylthio, azido, alkylcarbonyl, amino, aminocarbonyl, oxo, alkylsulphonyl, alkenylsulphonyl or aminosulphonyl by conversion to a leaving group and substitution by the required group, hydrolysis or oxidation as appropriate or reaction with an activated acid, isocyanate or alkoxyisocyanate. Primary and secondary hydroxy groups can be oxidised to an aldehyde or ketone respectively and alkyated with a suitable agent such as an organometalfic reagent to give a secondary or tertiary alcohol as appropriate. A carboxylate group may be converted to an hydroxymethyl group by reduction of an ester of this acid with a suitable reducing agent such as lithium aluminium hydride.

Substituted 2-oxo-oxazolidinyl containing $R^3$ groups may be prepared from the corresponding aldehyde by conventional reaction with a glycine anion equivalent, followed by cyclisation of the resulting amino alcohol M Grauert et al, Ann Chem (1985) 1817, Rozenberg et al, Angew Chem Int Ed Engl (1994) 33(1) 91). The resulting 2-oxo-oxazolidinyl group contains a carboxy group which can be converted to other $R^{10}$ groups by standard procedures.

Carboxy groups within $R^3$ may be prepared by Jones' oxidation of the corresponding alcohols CH$_2$OH using chromic acid and sulphuric acid in water/methanol (E. R. H. Jones et al, J. C. S. 1946, 39). Other oxidising agents may be used for this transformation such as sodium periodate catalysed by ruthenium trichloride (G. F. Tutwiler et al, J.Med.Chem., 1987, 30(6), 1094), chromium trioxide-pyridine (G. Just et al, Synth. Commun. 1979, 9(7), 613), potassium pennanganate (D. E. Reedich et al, J. Org. Chem., 1985, 50(19), 3535, and pyridinium chlorochromate (D. Askin et al, Tetrahedron Letters, 1988, 29(3), 277.

The carboxy group may alternatively be formed in a two stage process, with an initial oxidation of the alcohol to the corresponding aldehyde using for instance dimethyl sulphoxide activated with oxalyl chloride (N. Cohen et al, J. Am. Chem. Soc., 1983, 105, 3661) or dicyclohexylcarbodiimide (R. M. Wengler, Angew. Chim. Int. Ed. Eng., 1985, 24(2), 77), or oxidation with tetrapropylammonium perrhenate (Ley et al, J. Chem.Soc. Chem Commun.,1987, 1625). The aldehyde may then be separately oxidised to the corresponding acid using oxidising agents such as silver (II) oxide (R. Grigg et al, J. Chem. Soc. Perkin1, 1983, 1929), potassium permanganate (A. Zurcher, Helv. Chim. Acta., 1987, 70 (7), 1937), sodium periodate catalysed by ruthenium trichloride (T. Sakata et al, Bull. Chem. Soc. Jpn., 1988, 61(6), 2025), pyridinium chlorochromate (R. S. Reddy et al, Synth. Commun., 1988, 18(51), 545) or chromium trioxide (R. M. Coates et al, J. Am. Chem. Soc.,1982, 104, 2198).

An $R^3$ CO$_2$H group may also be prepared from oxidative cleavage of the corresponding diol, CH(OH)CH$_2$OH, using sodium periodate catalysed by ruthenium trichloride with an acetonitrile-carbontetrachloride-water solvent system (V. S. Martin et al, Tetrahedron Letters, 1988, 29(22), 2701).

$R^3$ groups containing a cyano or carboxy group may also be prepared by conversion of an alcohol to a suitable leaving group such as the corresponding tosylate by reaction with para-toluenesulphonyl chloride (M. R. Bell, J. Med. Chem., 1970, 13, 389), or the iodide using triphenylphosphine, iodine, and imidazole (G. Lange, Synth. Commun., 1990, 20, 1473). The second stage is the displacement of the leaving group with cyanide anion (L. A. Paquette et al, J. Org. Chem.,1979, 44 (25), 4603; P. A. Grieco et al, J. Org. Chem.,1988, 53 (16), 3658). Finally acidic hydrolysis of the nitrile group gives the desired acids (H. Rosemeyer et al, Heterocycles, 1985, 23 (10), 2669). The hydrolysis may also be carried out with base e.g. potassium hydroxide (H. Rapoport, S. Org. Chem.,1958, 23, 248) or enzymatically (T. Beard et al, Tetrahedron Asymmetry, 1993, 4 (6), 1085).

Other functional groups in $R^3$ may be obtained by conventional conversions of carboxy or cyano groups.

Tetrazoles are conveniently prepared by reaction of sodium azide with the cyano group (e.g. F. Thomas et al, Bioorg. Med. Chem. Lett., 1996, 6 (6), 631; K. Kubo et al, J. Med. Chem., 1993, 36, 2182) or by reaction of azidotri-n-butyl stannane with the cyano group followed by acidic hydrolysis (P. L. Omstein, J. Org. Chem., 1994, 59, 7682 and J. Med. Chem, 1996, 39 (11), 2219).

The 3-hydroxy-3-cyclobutene-1,2-dion-4-yl group (e.g. R. M. Soll, Bioorg. Med. Chem. Lett., 1993, 3 (4), 757 and W. A. Kinney, J. Med. Chem., 1992, 35 (25), 4720) can be prepared by the following sequence:—(1) a compound where R3 is (CH$_2$)$_n$CHO (n=0,1,2) is treated with triethylamine/carbon tetrabromide triphenylphosphine to give initially (CH$_2$)$_n$CH=CBr$_2$; (2) dehydrobronination of this intermediate to give the corresponding bromoethyne derivative (CH$_2$)$_n$C=CBr (for this 2 stage sequence see D. Grandjean et al, Tetrahedron Letters, 1994, 35 (21), 3529); (3) palladium-catalysed coupling of the bromoethyne with 4-(1-methylethoxy)-3-(tri-n-butylstannyl)cyclobut-3-ene-1,2-dione (Liebeskind et al, J. Org. Chem., 1990, 55, 5359); (4) reduction of the ethyne moity to —CH$_2$CH$_2$— under standard conditions of hydrogen and palladium on charcoal catalysis(see Howard et al, Tetrahedron, 1980, 36, 171); and finally (4) acidic hydrolysis of the methylethoxyester to generate the corresponding 3-hydroxy-3-cyclobutene-1,2-dione group (R. M. Soll, Bioorg. Med. Chem. Lett., 1993, 3 (4), 757).

The tetrazol-5-ylaminocarbonyl group may be prepared from the corresponding carboxylic acid and 2-aminotetrazole by dehydration with standard peptide coupling agents such as 1,1'-carbonyldiimidazole (P. L. Ornstein et al, J. Med Chem, 1996, 39 (11), 2232).

The alkyl- and alkenyl-sulphonylcarboxamides are similarly prepared from the corresponding carboxylic acid and the alkyl- or alkenyl-sulphonamide by dehydration with standard peptide coupling agents such as 1,1'-carbonyldiimidazole (P. L. Ornstein et al, J.Med.Chem., 1996, 39 (11), 2232).

The hydroxamic acid groups are prepared from the corresponding acids by standard amide coupling reactions eg N. R. Patel et al, Tetrahedron, 1987, 43 (22), 5375

2,4-thiazolidinedione groups may prepared from the aldehydes by condensation with 2,4-thiazolidinedione and subsequent removal of the olefinic double bond by hydrogenation.

The preparation of 5-oxo-1,2,4-oxadiazoles from nitriles is decribed by Y. Kohara et al, Bioorg. Med. Chem. Lett., 1995, 5(17), 1903.

1,2,4-triazol-5-yl groups may be prepared from the corresponding nitrile by reaction with an alcohol under acid conditions followed by reaction with hydrazine and then an $R^{10}$-substituted activated carboxylic acid (see J B Polya in 'Comprehensive Heterocyclic Chemistry' Edition 1 p762, Ed A R Katritzky and C W Rees, Pergamon Press, Oxford 1984 and J. J. Ares et al, J. Heterocyclic Chem., 1991, 28(5), 1197).

NH is converted to $NR^4$ by conventional means such as amide or sulphonamide formation with an acyl derivative $R^5V'COW$ or $R^5V'SO_2W$, for compounds where U is CO or $SO_2$ or, where U is $CH_2$, by alkylation with an alkyl halide $R^5$—V'—$CH_2$-halide or alkyl derivative $R^5$—V'—$CH_2$—W in the presence of base, acylation/reduction or reductive alkylation with an aldehyde $R^5$—V'—CHO where V' is V or a group convertible thereto such as a dimethyl acetal or 1,3-dithiane.

Where one of $R^3$ and $R^6$, $R^7$, $R^8$ or $R^9$ contains a carboxy group and the other contains a hydroxy or amino group they may together form a cyclic ester or amide linkage. This linkage may form spontaneously during coupling of the compound of formula (IV) and the piperidine moiety or in the presence of standard peptide coupling agents.

It will be appreciated that under certain circumstances interconvertions may interfere, for example, hydroxy groups in A or B and the piperidine NH will require protection e.g. as a carboxy- or silyl-ester group for hydroxy and as an acyl derivative for piperidine nitrogen, during conversion of $R^{1a'}$, $R^{1'}$, $R^{3'}$ or $R^{4'}$, or during the coupling of the compounds of formulae (IV) and (V).

Other routes to compounds of formula (I) include those via the intermediate of formula (VI):

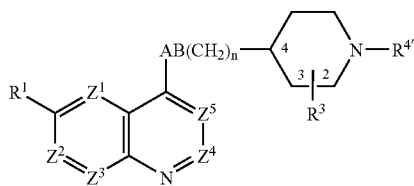

prepared by the routes described in WO99/37636, WO0/21948 and WO00/43383.

Compounds of formulae (IV) and (V) are known compounds, (see for example Smith et al, J. Amer. Chem. Soc., 1946, 68, 1301) or prepared analogously, see for example the references cited above.

Compounds of formula (V) where X is $CR^6R^7SO_2W$ may be prepared by a route analogous to that of Ahmed El Hadri et al, J. Heterocyclic Chem., 1993, 30(3), 631. Thus compounds of formula (IV) where X is $CH_2SO_2OH$ may be prepared by reacting the corresponding 4-methyl compound with N-bromosuccinimide, followed by treatment with sodium sulfite. The leaving group W may be converted to another leaving group W, e.g. a halogen group, by conventional methods.

The isocyanate of formula (IV) may be prepared conventionally from a 4-amino derivative such as 4-amino-quinoline, and phosgene, or phosgene equivalent (eg triphosgene) or it may be prepared more conveniently from a 4-carboxylic acid by a "one-pot" Curtius Reaction with diphenyl phosphoryl azide (DPPA) [see T. Shiori et al. Chem. Pharm. Bull. 35, 2698–2704 (1987)].

The 4-amino derivatives are commercially available or may be prepared by conventional procedures from a corresponding 4-chloro derivative by treatment with ammonia (O. G. Backeberg et. al., J. Chem Soc., 381, 1942) or propylamine hydrochloride (R. Radinov et. al., Synthesis, 886, 1986).

4-Alkenyl compounds of formula (IV) may be prepared by conventional procedures from a corresponding 4-halogeno-derivative by e.g. a Heck synthesis as described in e.g. Organic Reactions, 1982, 27, 345.

4-Halogeno derivatives of compounds of formula (IV) are commercially available, or may be prepared by methods known to those skilled in the art. A 4-chloroquinoline is prepared from the corresponding quinolin-4-one by reaction with phosphorus oxychloride ($POCl_3$) or phosphorus pentachloride, $PCl_5$. A-4-bromo-substituent may be prepared from the quinolin- or naphthyridin-4-one by reaction with phosphorus tribromide (PBr3) in DMF. A 4-chloroquinazoline is prepared from the corresponding quinazolin-4-one by reaction with phosphorus oxychloride ($POCl_3$) or phosphorus pentachloride, $PCl_5$. A quinazolinone and quinazolines may be prepared by standard routes as described by T. A. Williamson in Heterocyclic Compounds, 6, 324 (1957) Ed. R. C. Elderfield.

Activated carboxy derivatives X=A'COW of formula (IV) may be prepared from X=$A'CO_2H$ derivatives in turn prepared from $CO_2H$ derivatives by conventional methods such as homologation.

4-Carboxy derivatives of compounds of formula (IV) are commercially available or may be prepared by conventional procedures for preparation of carboxy heteroaromatics well known to those skilled in the art. For example, quinazolines may be prepared by standard routes as described by T. A. Williamson in Heterocyclic Compounds, 6, 324 (1957) Ed. R. C. Elderfield. These 4-carboxy derivatives maybe activated by conventional means, e.g. by conversion to an acyl halide or anhydride.

4-Carboxy derivatives such as esters may be reduced to hydroxymethyl derivatives with for example lithium aluminium hydride. Reaction with mesyl chloride and triethylamine would give the mesylate derivative. A diazo compound (X is —CH=$N_2$) may be prepared from the 4-carboxaldehyde via the tosyl hydrazone. The 4-carboxaldehyde may be obtained from the same hydroxymethyl derivative by oxidation with standard oxidising agents, eg manganese(II) dioxide.

A 4-oxirane derivative of compounds of formula (IV) is conveniently prepared from the 4-carboxylic acid by first conversion to the acid chloride with oxalyl chloride and then reaction with trimethylsilyldiazomethane to give the diazoketone derivative. Subsequent reaction with 5M hydrochloric acid gives the chloromethylketone. Reduction with sodium borohydride in aqueous methanol gives the chlorohydrin which undergoes ring closure to afford the epoxide on treatment with base, e.g. potassium hydroxide in ethanol-tetrahydrofuran.

Alternatively and preferably, 4-oxirane derivatives can be prepared from bromomethyl ketones which can be obtained from 4-hydroxy compounds by other routes well known to those skilled in the art. For example, hydroxy compounds can be converted to the corresponding 4-trifluoromethanesulphonates by reaction with trifluoromethanesulphonic anhydride under standard conditions (see K. Ritter, Synthesis, 1993, 735). Conversion into the corresponding butyloxyvinyl ethers can be achieved by a Heck reaction with butyl vinyl ether under palladium catalysis according to the procedure of W. Cabri et al, J. Org. Chem, 1992, 57 (5), 1481. (Alternatively, the equivalent intermediates can be attained by Stille coupling of the trifluoromethanesulphonates or the analaogous chloro derivatives with (1-ethoxyvinyl)tributyl tin, (T. R. Kelly, J. Org. Chem., 1996, 61, 4623.) The alkyloxyvinyl ethers are then converted into the corresponding bromomethylketones by treatment with N-bromosuccimimide in aqueous tetrahydrofuran in a similar manner to the procedures of J. F. W. Keana, J. Org. Chem., 1983, 48, 3621 and T. R Kelly, J. Org. Chem., 1996, 61, 4623.

The 4-hydroxyderivatives can be prepared from an aminoaromatic by reaction with methylpropiolate and subsequent cyclisation, analogous to the method described in N. E. Heindel et al, J. Het. Chem., 1969, 6, 77. For example, 5-amino-2-methoxy pyridine can be converted to 4-hydroxy-6-methoxy-[1,5]naphthyridine using this method.

If a chiral reducing agent such as (+) or (−)-B-chlorodiisopinocamphenylborane ['DIP-chloride'] is substituted for sodium borohydride, the prochiral chloromethylketone is converted into the chiral chlorohydrin with ee values generally 85–95% [see C. Bohm et al, *Chem. Ber.* 125, 1169–1190, (1992)]. Recrystallisation of the chiral epoxide gives material in the mother liquor with enhanced optical purity (typically ee 95%).

The (R)-epoxide, when reacted with an amine derivative gives ethanolamine compounds as single diastereomers with (R)-stereochemistry at the benzylic position.

Alternatively, the epoxide may be prepared from the 4-carboxaldehyde by a Wittig approach using trimethylsulfonium iodide [see G. A. Epling and K-Y Lin, *J. Het. Chem.*, 1987, 24, 853–857], or by epoxidation of a 4-vinyl derivative.

Pyridazines may be prepared by routes analogous to those described in Comprehensive Heterocyclic Chemistry, Volume 3, Ed A. J. Boulton and A. McKillop and napthyridines may be prepared by routes analogous to those described in Comprehensive Heterocyclic Chemistry, Volume 2, Ed A. J. Boulton and A. McKillop.

4-Hydroxy-1,5-naphthyridines can be prepared from 3-aminopyridine derivatives by reaction with diethyl ethoxymethylene malonate to produce the 4-hydroxy-3-carboxylic acid ester derivative with subsequent hydrolysis to the acid, followed by thermal decarboxylation in quinoline (as for example described for 4-Hydroxy-[1,5]naphthyridine-3-carboxylic acid, 3. T. Adams et al., *J.Amer.Chem.Soc.*, 1946, 68, 1317). A 4-hydroxy-[1,5]naphthyridine can be converted to the 4-chloro derivative by heating in phosphorus oxychloride, or to the 4-methanesulphonyloxy or 4-trifluoromethanesulphonyloxy derivative by reaction with methanesulphonyl chloride or trriluoromethanesulphonic anhydride, respectively, in the presence of an organic base. A 4-amino 1,5-naphthyridine can be obtained from the 4-chloro, 4-methanesulphonyloxy or 4-trifluoromethanesulphonyloxy derivative by reaction with n-propylamine in pyridine.

Similarly, 6-methoxy-1,5-naphthyridine derivatives can be prepared from 3-amino-6-methoxypyridine.

1,5-Naphthyridines may be prepared by other methods well known to those skilled in the art (for examples see P. A. Lowe in "Comprehensive Heterocyclic Chemistry" Volume 2, p581–627, Ed A. R. Katritzky and C. W. Rees, Pergamon Press, Oxford, 1984).

The 4-hydroxy and 4-amino-cinnolines may be prepared following methods well known to those skilled in the art [see A. R. Osborn and K. Schofield, *J. Chem. Soc.* 2100 (1955)].

For example, a 2-aminoacetophenone is diazotised with sodium nitrite and acid to produce the 4-hydroxycinnoline with conversion to chloro and amino derivatives as described for 1,5-naphthyridines.

The substituted piperidines of formula (V) are either commercially available or may be prepared by conventional methods.

For compounds of formula (V), where Y is $NHR^{11'}$ suitable amines may be prepared from the corresponding 4-substituted piperidine acid or alcohol. In a first instance, an N-protected piperidine containing an acid bearing substituent, can undergo a Curtius rearrangement and the intermediate isocyanate can be converted to a carbamate by reaction with an alcohol. Conversion to the amine may be achieved by standard methods well known to those skilled in the art used for amine protecting group removal. For example, an acid substituted N-protected piperidine can undergo a Curtius rearrangement e.g. on treatment with diphenylphosphoryl azide and heating, and the intermediate isocyanate reacts in the presence of 2-trimethylsilylethanol to give the trimethylsilylethylcarbamate (T. L. Capson & C. D. Poulter, *Tetrahedron Lett.*, 1984, 25, 3515). This undergoes cleavage on treatment with tetrabutylammonium fluoride to give the 4-amine substituted N-protected piperidine. Alternatively, an acid group $(CH_2)_{n-1}CO_2H$ may be converted to $(CH_2)_n NHR^{11}$ by reaction with an activating agent such as isobutyl chloroformate followed by an amine $R_{11}NH_2$ and the resulting amide reduced with a reducing agent such as $LiAlH_4$.

In a second instance, an N-protected piperidine containing an alcohol bearing substituent undergoes a Mitsunobu reaction (for example as reviewed in Mitsunobu, *Synthesis*, (1981), 1), for example with succinimide in the presence of diethyl azodicarboxylate and triphenylphosphine to give the phthalimidoethylpiperidine. Removal of the phthaloyl group, for example by treatment with methylhydrazine, gives the amine of formula (V).

Compounds of formula (V) where n=1 may be prepared from the compound where n=0 by homologation eg starting from a compound of formula (V) where $Y=CO_2H$.

Compounds of formula (V) with a —$CONHR^{11}$ group may be prepared from the corresponding nitrile by partial hydrolysis with with concentrated mineral acid at ambient temperature, such as concentrated hydrochloric acid (M. Brown et al, J. Med. Chem., 1999, 42, (9), 1537) or with concentrated sulphuric acid (F. Macias et al Tetrahedron, 2000, 56, (21), 3409).

Compounds of formula (V) with a —$OCONH_2$ group may be prepared from the corresponding alcohol by reaction with phosgene followed by ammonia Piperidines of formula (V) with substituents in the 2- or 3-positions may generally be prepared from the corresponding 2-, or 3-substituted 4-amino or 4-nitro-pyridine by hydrogenation over a catalyst such as palladium, usually at elevated temperatures and pressures.

Compounds of formula (V) with a $R^3$ 3-hydroxyl group may be prepared from commercially available starting materials such as 1-methyl-1,2,3,6-tetrahydro-pyridine-4-carboxylic acid ethyl ester. This may be demethylated with standard reagents such as 1-chloroethyl chloroformate and N-protected as a suitable carbamate, such as tert-butyloxycarbonyl or benzyloxycarbonyl. The olefin may be converted to the corresponding epoxide with standard agents such as hydrogen peroxide under basic catalysis, or meta-chloroperbenzoic acid. The alpha-epoxy ester may be reduced with reagents such as samarium(II) diiodide (see for instance Jones, P. G. et al, Tetrahedron Asymmetry, 1995, 6

(7), 1539) to give the 3-hydroxy-piperidine-4-carboxylic acid derivative. The alcohol can then be protected with for example triethylsilyl or tetrahydropyran-2-yl groups to give a suitably protected intermediate for conversion to compounds of formula (V) with a $R^3$ 3-hydroxyl group. $R^3$ 3-hydroxyl maybe derivatised or converted to amino by conventional procedures.

$R^5$—V'—$CH_2$-halides and $R^5$—V'—$CH_2$—W derivatives, acyl derivatives $R^5CH_2COW$ and $R^5CH_2SO_2W$ or aldehydes $R^5$—V'—CHO are commercially available or are prepared conventionally. The aldehydes may be prepared by partial reduction of the $R^5$—V'-ester with lithium aluminium hydride or di-isobutylaluminium hydride or more preferably by reduction to the alcohol, with lithium aluminium hydride or sodium borohydride (see *Reductions by the Alumino- and Borohydrides in Organic Synthesis*, 2nd ed., Wiley, N.Y., 1997; *JOC*, 3197, 1984; *Org. Synth. Coll.*, 102, 1990; 136, 1998; *JOC*, 4260, 1990; *TL*, 995, 1988; *JOC*, 1721, 1999; *Liebigs Ann./Recl.*, 2385, 1997; *JOC*, 5486, 1987), followed by oxidation to the aldehyde with manganese (II) dioxide, or by a 'Swern' procedure (oxalyl chloride/DMSO), or by using potassium dichromate (PDC). The aldehydes may also be prepared from carboxylic acids in two stages by conversion to a mixed anhydride for example by reaction with isobutyl chloroformate followed by reduction with sodium borohydride (R. J. Alabaster et al., Synthesis, 598, 1989) to give the alcohols and then oxidation with a standard oxidising agent such as pyridinium dichromate or by homologation of the $R^5CHO$ intermediate. Acyl derivatives $R^5CH_2COW$ maybe prepared by activation of the $R^5$—$CH_2$-ester. $R^5$—V'—$CH_2$-halides such as bromides may be prepared from the alcohol $R^5$—V'—$CH_2OH$ by reaction with phosphorus tribromide in DCM/triethylamine. $R^5$—V'—$CH_2$—W derivatives such as methanesulphonyl derivatives maybe prepared from the alcohol $R^5$—V'—$CH_2OH$ by reaction with methane sulphonyl chloride. $R^5CH_2SO_2W$ derivatives may be prepared by a route analogous to that of Ahmed El Hadri et al, *J. Heterocyclic Chem.*, 1993, 30(3), 631. Thus compounds of formula $R^5CH_2SO_2OH$ may be prepared by reacting the corresponding $R^5CH_3$ compound with N-bromosuccinimide, followed by treatment with sodium sulfite. The leaving group W may be converted to another leaving group W, e.g. a halogen group, by conventional methods. The $R^5$—V'—U— derivatives may be prepared by various conventional strategies. For example the homologous aldehyde $R^5$—CHO may be treated with trimethylsulfonium methylsulfate in basic conditions, to give an epoxide intermediate (see *Synth. Commun.*, 749, 1985) which is then treated with lewis acid, such as boron trifluorideetherate or diethyl etherate, to provide the desired aldehyde (see *JOC*, 1720, 1999). The aldehyde $R^5$—CHO could also be treated with an appropriate phosphonium salt, such as (methoxymethyl)triphenylphosphonium chloride, in a Wittig fashion reaction. The resulting enol ether can readily be hydrolysed to homologous aldehydes (*Chem. Ber.*, 2514, 1962). $R^5$—COW derivatives can be converted to the aldehyde $R^5$—V'—CHO in several steps (see *JACS*, 1325, 1986). The $R^5COCH_2$-halide derivatives may be prepared by standard methods from the $R^5CO_2H$ derivative, for example, by acid chloride formation, conversion to the alpha-diazoketone with diazomethane and reaction with a halogen acid to provide the halomethylketone.

Where $R^5$ is an optionally substituted benzoimidazol-2-yl group, the compound of formula (V) where $R^{4'}$ is $R^4$ may be obtained by reacting N protected piperidine with acrylonitrile, converting the resulting $R^{4'}$2-cyanoethyl group with partial hydrolysis to give the 2-ethoxycarbonimidoylethyl group which can then be condensed with an appropriately substituted 1,2-diaminobenzene to give the required benzoimidazol-2-yl group.

$R^5$—H heterocycles are commercially available or may be prepared by conventional methods.

For example where a benzoxazinone is required, a nitrophenol may be alkylated with for example ethyl bromoacetate and the resulting nitro ester reduced with Fe in acetic acid (alternatively Zn/AcOH/HCl or $H_2$/Pd/C or $H_2$/Raney Ni). The resulting amine may undergo spontaneous cyclisation to the required benzoxazinone, or cyclisation may be induced by heating in acetic acid. Alternatively a nitrophenol may be reduced to the aminophenol, which is reacted with chloroacetyl chloride [method of X. Huang and C. Chan, *Synthesis* 851 (1994)] or ethyl bromoacetate in DMSO [method of Z. Moussavi et al. *Eur. J. Med. Chim. Ther.* 24, 55–60 (1989)]. The same general routes can be applied to prepare benzothiazinones [See for example F. Eiden and F. Meinel, Arch. Pharm. 312, 302–312 (1979), H. Fenner and R Grauert *Liebigs. Ann. Chem.* 193–313 (1978)]. A variety of routes are available to prepare aza analogues of benzothiazinones via the key corresponding aldehydes. For instance, 2-oxo-2,3-dihydro-1H-pyrido[3,4-b][1,4]thiazine-7-carbaldehyde may be accessed from 5-fluoro-2-picoline (E. J. Blanz, F. A. French, J. R DoAmaral and D. A. French, J. Med. Chem. 1970, 13, 1124–1130) by constructing the thiazinone ring onto the pyridyl ring then functionalising the methyl substituent, as described in the Examples. The dioxin analogue of this aza substitution patem, 2,3-dihydro-[1,4]dioxino[2,3-c]pyridine-7-carbaldehyde is accessible from Kojic acid by aminolysis from pyrone to pyridone then annelating the dioxin ring, again as described in the subsequent experimental data. Other aza substitution patterns with pyridothiazin-3-one, pyridooxazin-3-one, and pyridodioxin ring systems are also accessible, again as descibed in the Examples. Ortho-aminothiophenols may be conveniently prepared and reacted as their zinc complexes [see for example V. Taneja et al *Chem. Ind.* 187 (1984)]. Benzoxazolones may be prepared from the corresponding aminophenol by reaction with carbonyl diimidazole, phosgene or triphosgene. Reaction of benzoxazolones with diphosporus pentasulfide affords the corresponding 2-thione. Thiazines and oxazines can be prepared by reduction of the corresponding thiazinone or oxazinone with a reducing agent such as lithium aluminium hydride.

Conversions of $R^{1a'}$, $R^{1'}$, $R^{3'}$ and $R^{4'}$ may be carried out on the intermediates of formulae (IV) and (V) prior to their reaction to produce compounds of formula (I) in the same way as described above for conversions after their reaction.

The pharmaceutical compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable salt or in vivo hydrolysable ester thereof is administered in the above-mentioned dosage range.

The compound of formula (I) may be the sole therapeutic agent in the compositions of the invention or a combination with other antibiotics or with a β-lactamase inhibitor may be employed.

Compounds of formula (I) are active against a wide range of organisms including both Gram-negative and Gram-positive organisms.

The following examples illustrate the preparation of certain compounds of formula (I) and the activity of certain compounds of formula (I) against various bacterial organisms.

EXAMPLES

Example 1

1-[2-(3-Oxo-3,4-dihydro-2H-benzo[1,4]thiazin-6-yl)-ethyl]-piperidine-4-carboxylic acid (6methoxy-[1,5]naphthyridinylaramide oxalate

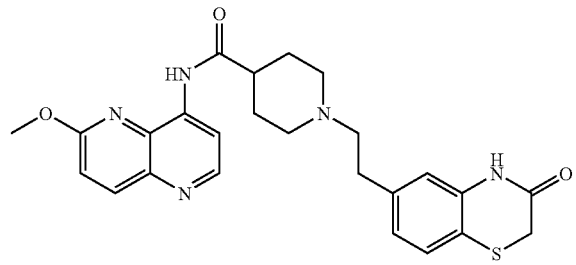

(a) 6-Methoxy-1H-[1,5]naphthyridin-4-one

A solution of 5-amino-2-methoxypyridine (50 g, 0.4 mol) in ethanol (300 ml) was treated with 2,2-dimethyl-[1,3]dioxane-4,6-dione (Meldrum's acid) (68 g) and triethylorthoformate (66 ml). The mixture was heated to reflux for 2 hours, then allowed to cool. Filtration afforded the intermediate 5-[(6-methoxy-pyridin-3-ylamino)-methylene]-2,2-dimethyl-[1,3]dioxane-4,6-dione as a white solid (101.2 g). A portion of this material (50 g) was added to boiling Dowtherm A (300 ml) over 3 minutes under a stream of argon. The mixture was refluxed for a further 5 minutes then allowed to cool before adding to ether. Filtration and drying afforded 6-methoxy-1H-[1,5]naphthyridin-4-one as a white solid (24.7 g, 70%).

MS (+ve ion electrospray) m/z 177 (MH+).

(b) 1,1,1-Trifluoro-methanesulfonic acid 6-methoxy-[1,5]naphthyridin-4-yl ester

A suspension of naphthyridone (a) (10 g, 0.057 mol) in dichloromethane (200 ml) containing 2,6-lutidine (9.94 ml, 86 mmol) and 4-dimethylaminopyridine (0.07 g, 5.7 mol) was cooled in ice and treated with trifluoromethanesulfonic anhydride (10.5 ml, 63 mmol). After stirring for 2.5 hours the mixture was washed with saturated ammonium chloride solution, dried, evaporated and purified on silica eluting with dichloromethane affording the triflate as an oil (13.4 g, 76%).

MS (+ve ion electrospray) m/z 309 MH+).

(c) 6-Methoxy-[1,5]naphthyridin-4-ylamine

A mixture of triflate (b) (25 g, 81.2 mmol) and propylamine hydrochloride (47 g, 487 mmol) in pyridine (300 ml) was heated to reflux overnight. The mixture was evaporated to dryness, dissolved in 0.5M aqueous hydrochloric acid (400 ml) and extracted three times with dichloromethane. The aqueous phase was then basified with 40% aqueous sodium hydroxide solution and extracted twice with dichloromethane. Drying and evaporation afforded a buff coloured solid (13.0 g, 90%).

MS (+ve ion electrospray) m/z 176 (MH+).

(d) Piperidine-1,4-dicarboxylic acid benzyl ester

A solution of piperidine-4-carboxylic acid (4.7 g, 36 mmol) in 0.5M aqueous sodium hydroxide (160 ml, 80 mmol) and dioxan (50 ml) was treated with benzyl chloroformate (4.3 ml, 5.13 g, 30 mmol). After 1 hour the mixture was acidified with 5M aqueous hydrochloric acid and extracted twice with ethyl acetate. The combined organic extracts were washed with water and brine, then dried and evaporated affording an oil (7.9 g, 100%).

MS (+ve ion electrospray) m/z 264 (MH+).

(e) 4-(6-Methoxy-[1,5]naphthyridin-4-ylcarbamoyl)-piperidine-1-carboxylic acid benzyl ester A solution of acid (d) (7.9 g, 30 mmol) and triethylamine (4.2 ml, 3.03 g, 30 mmol) in N,N-dimethylformamide (50 ml) was treated with [O-(7-azabenzotriazol-1-yl)-1,1,3,3-tetramethyluronium hexafluorophosphate] (HATU) (9.5 g, 25 mmol). After 0.25 hours, amine (c) (3.5 g, 20 mmol) was added and the mixture heated at 50° C. overnight. Evaporation afforded an oil which was partitioned between ethyl acetate and dilute brine. Drying and evaporation afforded an oil (10 g) which was chromatographed on silica eluting with a 0–5% methanol in ethyl acetate gradient, affording an oil (6.0 g, 80%).

MS (+ve ion electrospray) m/z 421 (MH+).

(f) Piperidine-4-carboxylic acid (6-methoxy-[1,5]naphthyridin-4-yl)-amide

A solution of (e) (6.0 g, 14.3 mmol) in ethanol/ethyl acetate (150 ml/150 ml) was hydrogenated over 10% Pd/charcoal (5 g) for 1.5 hours. Filtration, washing with ethanol (400 ml) and evaporation of the filtrate gave a white solid (2.4 g, 59%).

MS (+ve ion electrospray) m/z 287 (MH+).

(g) [4-(2-Hydroxy-ethyl)-2-nitro-phenylsulfanyl]-acetic acid.

A mixture of 2-(4-fluoro-3-nitro-phenyl)ethanol [RN20274-69-5](1.1 g, 6 mmol), mercaptoacetic acid (0.61 g, 6.6 mmol), potassium carbonate (2.8 g, 20 mmol) and N,N-dimethylformamide (12 ml) was heated at 70° C. for 4 hours. The mixture was poured onto water (200 ml) and the aqueous phase was washed with ethyl acetate. The aqueous phase was then acidified with 1M aqueous hydrochloric acid and extracted three times with dichloromethane. The extracts were dried and evaporated to give an oil (0.92 g, 60%).

δH (d-6 DMSO, 200 MHz): 8.07 (1H, d), 7.60 (1H, dd), 7.50 (1H, d), 3.92 (2H, s), 3.63 (2H, t), 3.50 (2H, br), 2.79 (2H, t).

(h) 6-(2-Hydroxy-ethyl)-4H-benzo[1,4]thiazin-3-one.

A mixture of iron powder (1.24 g, 22 mmol) and sodium chloride (1.24 g, 21 mmol) in 50% aqueous ethanol (25 ml) was heated under reflux for 15 minutes. A solution of crude (g) (0.92 g, 3.6 mmol) in ethanol (5 ml) was then added quickly and the reaction mixture was heated under reflux for 2 hours. The mixture was filtered through keiselguhr and the solution was evaporated to dryness. The residue was dissolved in water and acidified to pH5 with 1M aqueous hydrochloric acid. The precipitate was collected by filtration, washed with water, then dried to give a white solid (0.35 g, 46%).

δH (d-6 DMSO, 200 MHz): 10.48 (1H, br), 7.20 (1H, d), 6.92–6.87 (2H, m), 4.65 (1H, t), 3.56 (2H, q), 3.42 (2H, s), 2.64 (2H, t).

(i) Methanesulfonic acid 2-(3-oxo-3,4dihydro-2H-benzo[1,4]thiazin-6-yl)-ethyl ester A solution of (h) (0.34 g, 1.7 mmol) and triethylamine (0.25 ml, 0.19 g, 1.8 mmol) in dichloromethane (5 ml) was cooled to −15° C. and treated dropwise with methanesulfonyl chloride (0.14 ml, 1.75 mmol). The ice bath was removed and the mixture stirred 15 hours at room temperature. The organic phase was separated, washed with water, dried over magnesium sulfate and evaporated. The crude product was chromatographed on silica gel eluting with ethyl acetate/heptane (2/1) to give a white solid (0.36 g, 75%).

δH (d-6 DMSO, 200 MHz): 10.55 (1H, br), 7.27 (1H, d), 6.92 (1H, dd), 6.87 (1H, d), 4.37 (2H, t), 3.45 (2H, s), 3.13 (3H, s), 2.93 (2H, t).

(j) Title Compound

A mixture of amine (f) (0.15 g, 0.52 mmol), mesylate (i) (0.158 g, 0.55 mmol) and potassium carbonate (0.076 g, 0.55 mmol) in N,N-dimethylformamide (3 ml) was stirred at 40° C. for 8 hours. The mixture was diluted with water and ethyl acetate. The insoluble residue was collected by filtration, washed with water and ethyl acetate, then dried to give the free base of the title compound as a white solid (0.15 g, 25%).

δH (d-6 DMSO, 200 MHz): 10.62 (1H, br), 9.91 (1H, br), 8.70 (1H, d), 8.40 (1H, d,), 8.28 (1H, d), 7.42–7.24 (2H, m), 7.00–6.78 (2H, m), 4.15 (3H, s), 3.60 (2H, m), 3.44 (2H, s), 3.22 (2H, m), 3.13–2.81 (5H, m), 2.30–1.85 (4H, m). MS (+ve ion electrospray) m/z 478 (MH+).

A suspension of the above solid (55 mg, 0.12 mmol) in acetone was treated with a solution of oxalic acid (22 mg) in acetone and the mixture was stirred for 2 hours. The precipitate was collected by filbation to give the title compound as white crystals (58 mg).

Example 2

1-(2-Benzo[1,3]dioxol-5yl-ethyl)-piperidine4-carboxylic acid (6-methoxy-[1,5]naphthyridin-4-yl) amide, dioxalate

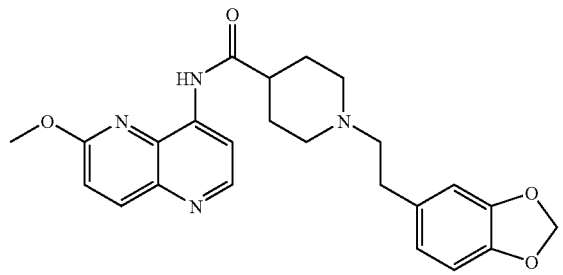

(a) 2-Benzo[1,3]dioxol-5-yl-ethanol

A solution of benzo[1,3]dioxol-5-yl-acetic acid (2.5 g, 13.9 mmol) in tetrahydrofuran (15 ml) under argon at −10° C. was treated dropwise with borane-dimethylsulfide complex (1.45 ml, 15.3 mmol). The mixture was stirred at ambient temperature for 1.5 hours (CAUTION—exothermic reaction). The orange solution was cooled to ~5° C. (ice bath) and methanol (1.4 ml) was added. After 0.5 hour at room temperature, the mixture was partitioned between ethyl acetate and saturated aqueous sodium bicarbonate solution. The organic extract was dried and evaporated to give a yellow oil (1.95 g, 84%).

MS (+ve ion electrospray) m/z 167 (MH+).

(b) Methanesulfonic acid 2-benzo[1,3]dioxol-5-yl-ethyl ester

A solution of alcohol (a) (1.90 g, 11 mmol) in dichloromethane (25 ml) was treated at 0° C. with triethylamine (1.9 ml, 13.7 mmol) and methanesulfonyl chloride (1.1 ml, 13.7 mmol). After 1.5 hours at room temperature the mixture was partitioned between dichloromethane and water. The organic extract was dried and evaporated to give a yellow oil (2.7 g, 96%).

MS (+ve ion electrospray) m/z 245 (MH+).

(c) Title Compound

This was prepared from amine (1f) (0.15 g), mesylate (b) (0.134 g) and potassium carbonate (0.076 g) in N,N-dimethylformamide (3 ml) at 50° C. for 6 hours in a similar procedure to that of Example (1j). The solvent was evaporated in vacuo and the residue was dissolved in ethyl acetate, washed with water, dried over magnesium sulfate and evaporated to dryness. The residue was chromatographed on silica gel eluting with ethyl acetate/methanol (95/5) to give the free base of the title compound as an oil (70 mg, 31%).

δH (d-6 DMSO, 200 MHz): 9.91 (1H, br), 8.70 (1H, d), 8.40 (1H, d), 8.28 (1H, d), 7.33 (1H, d), 6.94–6.85 (2H, m), 6.76 (1H, dd), 6.00 (2H, s), 4.16 (3H, s), 3.58 (2H, m), 3.23 (2H, m), 3.17–2.83 (5H, m), 2.29–1.88 (4H, m).

MS (+ve ion electrospray) m/z 435 (MH+).

This was converted to the title compound (61 mg) by treating with oxalic acid in acetone according to the procedure for Example 1.

Example 3

1-[2-(2,3-Dihydro-benzo[1,4]dioxin-6-yl)-ethyl]-piperidine-4-carboxylic acid (6-methoxy-[1,5]naphthyridin-4-yl)-amide, dioxalate

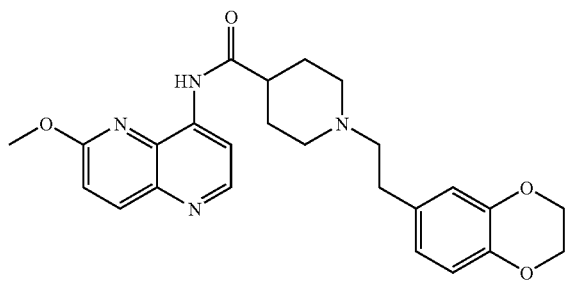

(a) 6-Oxiranyl-2,3-dihydro-benzo[1,4]dioxine

A mixture of 1,4-benzodioxanecarboxaldehyde [RN 29668-44-8](1.5 g, 9.14 mmol), trimethylsulfonium methyl sulfate (2.24 g, 11.9 mmol), dichloromethane (35 ml) and 50% aqueous sodium hydroxide (5 ml) were vigorously stirred for 70 hours. The mixture was partitioned between water and diethyl ether and the layers separated. The aqueous phase was extracted with diethyl ether. The combined organic phases were washed with water, brine, then dried over magnesium sulfate and evaporated to give crude 6-oxiranyl-2,3-dihydro-benzo[1,4]dioxine (1.64 g, 100%).

δH (CDCl3, 200 MHz): 6.88–6.72 (3H, m), 4.25 (4H, s), 3.76 (1H, dd), 3.10 (1H, dd), 2.77 (1H, dd).

(b) (2,3-Dihydro-benzo[1,4]dioxin-6-yl)-acetaldehyde.

A solution of crude 6-oxiranyl-2,3-dihydro-benzo[1,4] dioxine (200 mg, 1.12 mmol) in diethyl ether (20 ml) was cooled at −10° C. A 10% solution of boron trifluoride diethyl etherate in diethyl ether (0.16 ml) was then added and the mixture was stirred for 10 minutes at −10° C. The reaction was quenched at this temperature by addition of a saturated aqueous solution of sodium bicarbonate (10 ml). The mixture was extracted twice with diethyl ether. The combined organic phases were washed with water, brine, then dried over magnesium sulfate and evaporated to give crude (2,3-dihydro-benzo[1,4]dioxin-6-yl)-acetaldehyde (191 mg, 95%).

δH (CDCl3, 200 MHz): 9.70 (1H, t), 6.95–6.62 (3H, m), 4.26 (4H, s), 3.56 (2H, d).

(c) Title Compound

A solution of amine (1f) (238 mg, 0.83 mmol) and crude aldehyde (3b) (191 mg, 1.07 mmol) in methanol (20 ml) was acidified to pH5 with a few drops of acetic acid then sodium cyanoborohydride (42 mg, 0.67 mmol) was added and the mixture was stirred for 20 hours. The solvent was evaporated and the residue was triturated with ethyl acetate (10 ml) and 0.1M aqueous sodium hydroxide solution (10 ml). The mixture was filtered and the layers of the filtrate were separated. The aqueous phase was extracted with more ethyl acetate. The combined organic extracts were washed with water, dried over magnesium sulfate and evaporated to give a solid (0.2 g). This solid was triturated with heptane-ethyl acetate (2–1) to give the free base of the title compound (85 mg, 23%).

δH (d-6 DMSO, 200 MHz): 9.79 (1H, br), 8.67 (1H, d), 8.41 (1H, d), 8.27 (1H, d), 7.32 (1H, d), 6.81–6.60 (3H, m), 4.20 (4H, s), 4.13 (3H, s), 2.99 (2H, m), 2.82–2.48 (5H, m), 2.15–1.85 (4H, m), 1.84–1.58 (2H, m).

MS (+ve ion electrospray) m/z 449 (MH+).

This was converted to the title compound (112 mg) by treating with oxalic acid in acetone according to the procedure for Example 1.

Example 4

1-[2-(4-Fluoro-1H-benzoimidazol-2-yl)-ethyl]-piperidine-4-carboxylic acid (6-methoxy-[1,5]naphthyridin-4-yl)-amide, dioxalate

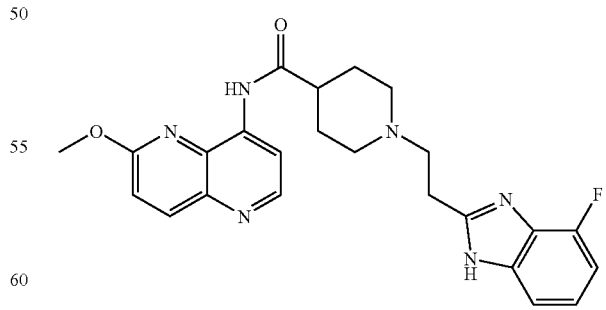

(a) 1-(2-Cyano-ethyl)-piperidine-4-carboxylic acid ethyl ester

A solution of piperidine-4-carboxylic acid ethyl ester (ethylisonipecotate) (4.7 g, 30 mmol), acrylonitrile (1.7 g, 31 mmol) in isopropyl alcohol (30 ml) was stirred at room temperature for 15 hours, then evaporated to dryness to afford 1-(2-cyano-ethyl)-piperidine-4-carboxylic acid ethyl ester as an oil (6.4 g, 100%).

δH (CDCl3, 200 MHz): 4.13 (2H, q), 2.94–2.78 (2H, m), 2.75–2.62 (2H, m), 2.55–2.43 (2H, m), 2.27 (1H, m), 2.14 (2H, m), 1.99–1.62 (4H, m), 1.25 (3H, t).

(b) 1-[2-(4-Fluoro-1H-benzoimidazol-2-yl)-ethyl]-piperidine-4-carboxylic acid ethyl ester A solution of (a) (6.4 g, 30 mmol) and ethanol (2.1 ml, 40 mmol) in chloroform (60 ml) was saturated with gaseous hydrochloric acid at 0° C. for 0.5 hours. The mixture was left 20 hours at 4° C. then concentrated in vacuo to afford a white foam. This was suspended in chloroform (60 ml), treated with 3-fluorophenylenediamine (3.8 g, 30 mmol) and heated under reflux for 1 hour. The mixture was poured onto water. The aqueous phase was then basified with sodium bicarbonate and extracted three times with dichloromethane. The organic extract was washed with water, brine, dried over magnesium sulfate and evaporated. The resulting residue was triturated with ethyl acetate, then diethyl ether to give a white solid (5.2 g, 55%).

δH (CDCl3, 200 MHz): 7.29 (1H, d), 7.21–7.05 (1H, m), 7.00–6.82 (1H, m), 4.17 (2H, q), 3.12–2.95 (4H, m), 2.88 (1H, br), 2.80 (2H, t), 2.42 (1H, m), 2.31–1.73 (6H, m), 1.29 (3H, t).

(c) 1-[2-(4-Fluoro-1H-benzoimidazol-2-yl)-ethyl]-piperidine-4-carboxylic acid.

A solution of (b) (2.0 g, 6.3 mmol), 1M aqueous sodium hydroxide solution (1.2 ml, 1.2 mmol) in ethanol (40 ml) was stirred at room temperature for 3 hours. After concentration, the residue was diluted with water and acidified with a saturated solution of potassium hydrogenosulfate to pH 5. The precipitated solid was filtered, washed with water and dried under vacuum to afford a foam (1.0 g, 54%).

δH (d-6 DMSO, 200 MHz): 7.28 (1H, d), 7.21–7.02 (1H, m), 7.00–6.81 (1H, m), 3.41 (2H, br), 3.10–2.62 (6H, m), 2.33–1.95 (3H, m), 1.94–1.68 (2H, m), 1.65–1.40 (2H, m).

(d) Title Compound

A mixture of (c) (291 mg, 1 mmol), [O-(7-azabenzotriazol-1-yl)-1,1,3,3-tetramethyluronium hexafluorophosphate] (HATU) (570 mg, 1.5 mmol), amine (1c) (0.176 g, 1 mmol) and triethylamine (0.21 ml, 1.5 mmol) in tetrahydrofuran/dichloromethane (15 ml/12 ml) was stirred at room temperature for 16 hours. After concentration, the residue was heated in dimethylsulfoxide (8 ml) for 4 hours, then poured into water, basified with 1M aqueous sodium hydroxide, and extracted three times with dichloromethane. The organic phase was washed with water, brine, dried over magnesium sulfate and evaporated. The product was purified by column chromatography on silica gel, eluting with ethyl acetate-methanol (9:1) to afford the free base of the title compound as a white solid (90 mg, 20%).

δH (d-6 DMSO, 200 MHz): 12.5 (1H, br), 9.78 (1H, s), 8.67 (1H, d), 8.41 (1H, d), 8.26 (1H, d), 7.38–7.23 (2H, m), 7.10 (1H, m), 6.92 (1H, dd), 4.13 (3H, s), 3.10–2.91 (4H, m), 2.90–2.62 (3H, m), 2.22–2.03 (2H, m), 2.01–1.87 (2H, m), 1.86–1.55 (2H, m).

MS (+ve ion electrospray) m/z 449 (MH+).

This was converted to the title compound (60 mg) by treating with oxalic acid in acetone according to a similar procedure as for Example 1.

Example 5

1-(2-Benzo[1,2,5]thiadiazol-5-yl-ethyl)-piperidine-4-carboxylic acid (6-methoxy-[1,5]naphthyridin-4-yl)-amide, dioxalate

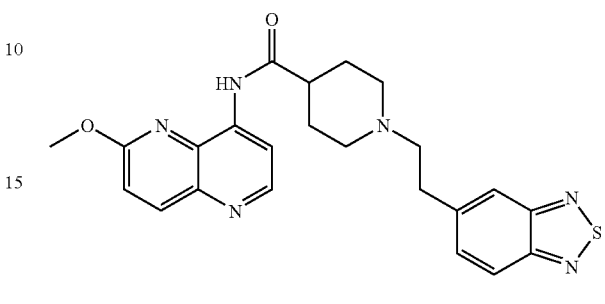

(a) Benzo[1,2,5]thiadiazol-5-yl-acetonitrile

A mixture of 5-bromomethyl-benzo[1,2,5]thiadiazole [RN65858-50-6](7.0 g, 30 mmol), ethanol (50 ml)and a solution of potassium cyanide (2.3 g, 36 mmol) in water (25 ml) was stirred at 50° C. for 15 hours. The alcoholic solution was concentrated and the residue suspended in water. The solid was collected by filtration, washed with water and dried in vacuo to give benzo[1,2,5]thiadiazol-5-yl-acetonitrile (2.8 g, 47%)

(b) Benzo[1,2,5]thiadiazol-5-yl-acetic acid

A suspension of benzo[1,2,5]thiadiazol-5-yl-acetonitrile (a) (2.8 g, 14 mmol) in 6N aqueous hydrochloric acid (70 ml) was heated under reflux for 4 hours. The mixture was cooled to room temperature and diluted with more water. The precipitate was collected by filtration, washed with water and dried in vacuo to give crude benzo[1,2,5]thiadiazol-5-yl-acetic acid (2.8 g, 100%).

δH(DMSO-d6, 200 MHz): 12.58 (1H, br), 8.03 (1H, d), 7.97 (1H, d), 7.65 (1H, dd), 3.86 (2H, s).

(c) 2-Benzo[1,2,5]thiadiazol-5-yl-ethanol.

Borane methylsulfide (1.6 ml) was added dropwise to a cold solution (8–10° C.) of crude benzo[1,2,5]thiadiazol-5-yl-acetic acid (b) (2.8 g, 14 mmol) in tetrahydrofuran (20 ml). Stirring was continued for 1.25 hours while maintaining the temperature below 30° C. The mixture was cooled to 10° C. then methanol was added (1.4 ml) and the mixture was left 15 hours in the refrigerator. The mixture was diluted with ethyl acetate, washed with water then with a saturated aqueous solution of sodium hydrogencarbonate and again with water. The organic phase was separated, dried over magnesium sulfate and evaporated. The residue was triturated in pentane, collected by filtration and dried to give crude 2-benzo[1,2,5]thiadiazol-5-yl-ethanol (1.8 g, 71%).

δH(CDCl3, 200 MHz): 7.94 (1H, d), 7.84 (1H, d), 7.50 (1H, dd), 3.99 (2H, t), 3.06 (2H, t), 1.58 (1H, br).

(d) Methanesulfonic acid 2-benzo[1,2,5]thiadiazol-5-yl-ethyl ester.

Methanesulfonyl chloride (0.45 ml, 5.8 mmol) was added dropwise to an ice-cooled solution of 2-benzo[1,2,5]thiadiazol-5-yl-ethanol (c) (1.0 g, 5.5 mmol) and triethylamine (0.85 ml, 6 mmol) in dichloromethane (20 ml) The reaction mixture was allowed to warn to room temperature and stirred for 16 hours. The organic solution was washed with water, dried over magnesium sulfate and evaporated to dryness. The oily residue was triturated with diisopropyl ether. The solid was collected by filtration and dried to give methanesulfonic acid 2-benzo[1,2,5]thiadiazol-5-yl-ethyl ester (1.2 g, 78%) which was used without further purification in the next step.

(e) Title Compound.

A mixture of piperidine-4carboxylic acid (6-methoxy-[1,5]naphthyridin-4-yl)-amide (1f) (0.2 g, 0.7 mmol), mesylate (d) (0.2 g, 0.77 mmol), triethylamine (0.11 ml) and acetonitrile (12 ml) was heated under reflux for 16 hours. After cooling to room temperature the mixture was poured onto water and extracted with ethyl acetate. The organic phase was washed with water, dried over magnesium sulfate and evaporated to dryness. The crude product was chromatographed on silica gel eluting with methylene chloride-methanol (95-5). The product was triturated in ethyl acetate and filtered to give the free base of the title compound as a solid (0.16 g, 41%).

δH(d-6 DMSO, 200MHz): 9.78 (1H, s), 8.67 (1H, d), 8.40 (1H, d), 8.26 (1H, d), 8.01 (1H, d), 7.93 (1H, d), 7.66 (1H, dd), 7.31 (1H, d), 4.13 (3H, s), 3.15–2.90 (4H, m), 2.86–2.08 (3H, m), 2.11 (2H, m), 1.95 (2H, m), 1.72 (2H, m).

This was converted to the title compound (130 mg) by treating with oxalic acid in acetone according to the procedure for Example 1, mp : 228–230° C.

Example 6

1-[2-(3-Methyl-2-oxo-2,3-dihydro-benzooxazol-6-yl)-ethyl]-piperidine-4-carboxylic acid (6-methoxy-[1,5]naphthyridin-4-yl)-amide, dioxalate

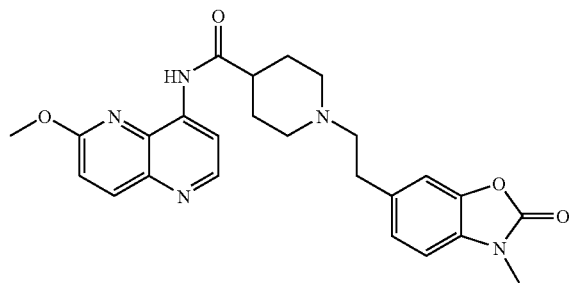

(a) 6-(2-Hydroxy-ethyl)-3-methyl-3H-benzooxazol-2-one.

Borane dimethylsulfide complex (10M; 1.1 ml, 11 mmol) was added dropwise to a cold suspension (10° C.) of (3-methyl-2-oxo-2,3-dihydro-benzooxazol-6-yl)-acetic acid [RN245095-56-1](2.1 g, 10 mmol) in anhydrous tetrahydrofuran (20 ml). The reaction temperature was allowed to rise progressively to 28–29° C. After 1 hour the temperature began to decrease. Stiring was maintained for a further 0.5 hour, then the mixture was cooled to 10° C. and treated dropwise with methanol (1 ml). Stirring was continued, at room temperature, for another 0.5 hour. The reaction mixture was concentrated and the residue was suspended in water and the aqueous phase was acidified by 0.1 N hydrochloric acid. The solid (unreacted starting acid) was filtered off. The aqueous phase was extracted three time with dichloromethane. The extract was dried over magnesium sulfate and evaporated. The crude residue was chromatographed on silica gel eluting with dichloromethane-methanol (95-5) to give the product (0.78 g, 80% based on reacted acid).

δH(CDCl3, 200 MHz): 7.10 (1H, d), 7.07 (1H, dd), 6.89 (1H, d), 3.86 (2H, t), 3.39 (3H, s), 2.90 (2H, t).

(b) Methanesulfonic acid 2-(3-methyl-2-oxo-2,3dihydro-benzooxazol-6-yl)-ethyl ester.

Methanesulfonyl chloride (0.14 ml, 1.75 mmol) was added dropwise to an ice cooled solution of (6a) (325 mg, 1.7 mmol) and triethylamine (0.25 ml, 1.8 mmol) in dichloromethane (5 ml). The reaction mixture was allowed to warm to room temperature and stirred for 15 hours. The organic solution was washed with water, dried over magnesium sulfate and evaporated to dryness. The residue was triturated with diisopropyl ether. The solid was collected by filtration and dried to give the product (410 mg, 89%)

δH(CDCl3, 200 MHz): 7.14–7.02 (2H, m), 6.91 (1H, d), 4.40 (2H, t), 3.40 (3H, s), 3.09 (2H, t), 2.93 (3H, s).

(c) Title Compound.

A mixture of amine (1f) (0.2 g, 0.7 mmol), mesylate (b) (0.19 g, 0.7 mmol), triethylamine (0.11 ml) and acetonitrile (12 ml) was heated under reflux for 20 hours. After cooling the mixture was poured onto water and extracted twice with dichloromethane. The organic phase was washed with water, dried over magnesium sulfate and evaporated to dryness. The crude product was chromatographed on silica gel eluting with methylene chloride-methanol (95–5). to give the free base of the title compound (0.115 g, 35%) as a solid.

δH(d-6 DMSO, 200 MHz): 9.78 (1H, s), 8.67 (1H, d), 8.40 (1H, d), 8.26 (1H, d), 7.31 (1H, d), 7.24 (1H, d), 7.20–7.02 (2H, m), 4.13 (3H, s), 3.29 (3H, s), 3.00 (2H, m), 2.87–2.63 (3H, m), 2.53 (2H, m), 2.20–1.54 (6H, m).

This was converted to the title compound (131 mg) by treating with oxalic acid in acetone according to the procedure for Example 1, mp : 226–228° C.

Example 7

1-[2-(3-Oxo-3,4-dihydro-2H-benzo-[1,4]oxazin-6-yl)ethyl]-piperidine-4-carboxylic acid (6-methoxy-[1,5]naphthyridin-4-yl)-amide, dioxalate

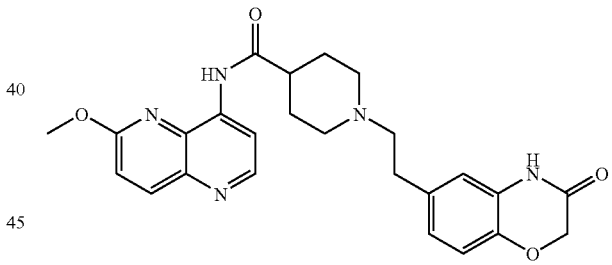

(a) 6-(2-Hydroxy-ethyl)-4H-benzo[1,4]oxazin-3-one.

Lithium aluminium hydride (0.7 g, 14.6 mmol) was added portionwise to an ice-cooled solution of (3-oxo-3,4-dihydro-2H-benzo[1,4]oxazin-6-yl)-acetic acid tert-butoxycarbonylmethyl ester [RN134997-90-3](4.5 g, 14 mmol) in tetrahydrofuran (100 ml). The mixture was allowed to warm to room temperature and stirring was maintained for 1 hour. The excess of hydride was hydrolysed by careful addition of a saturated aqueous solution of ammonium chloride (10 ml). The mixture was filtered and the filtrate was evaporated. The residue was triturated with diisopropyl ether to give the product (2.15 g, 80%).

δH(CDCl3, 200 MHz): 10.63 (1H, s), 6.85–6.70 (3H, m), 4.62 (1H, t), 4.51 (2H, s), 3.53 (2H, t), 2.62 (2H, t).

(b) Methanesulfonic acid 2-(3-oxo-3,4-dihydro-2H-benzo[1,4]oxazin-6-yl)-ethyl ester.

A solution of alcohol (a) (0.65 g, 3.38 mmol) and triethylamine (0.52 ml, 3.72 mmol) in tetrahydrofuran (30 ml) was cooled to −10° C. and treated dropwise by methanesulfonyl chloride (0.26 ml, 3.6 mmol). The ice bath was removed and the mixture stirred 20 hours at room temperature. More triethylamine (0.6 ml) and methane sulfonyl chloride (0.3 ml) were added at 0° C. and the mixture stirred for a further 2 hours. The mixture was diluted with ethyl acetate and washed with water. The organic phase was dried over magnesium sulfate and evaporated. The crude product was chromatographed on silica gel eluting with methylene chloride-methanol (98-2) to give the product (0.85 g, 92%).

δH(CDCl3, 200 MHz): 8.63 (1H, s), 6.91 (1H, s), 6.87 (1H, d), 6.72 (1H, d), 4.61 (2H, s), 4.41 (2H, t), 3.01 (2H, t), 2.94 (3H, s).

(c) Title Compound.

A mixture of amine (1f) (0.58 g, 2 mmol), mesylate (b) (0.6 g, 2.2 mmol), potassium carbonate (0.3 g, 2.2 mmol) and acetonitrile (40 ml) was heated under reflux for 6 hours and stirred at room temperature for 48 hours. The mixture was poured into water and extracted twice with dichloromethane. The organic phase was washed with water, dried over magnesium sulfate and evaporated to dryness. The crude product was chromatographed on silica gel eluting with dichloromethane-methanol (98-2) to give the free base of the title compound (0.25 g, 27%).

δH(d-6 DMSO, 200 MHz): 10.65 (1H, br), 9.79 (1H, s), 8.68 (1H, d), 8.41 (1H, d), 8.27 (1H, d), 7.31 (1H, d), 6.93–6.70 (3H, m), 4.52 (2H, s), 4.14 (3H, s), 3.01 (2H, m), 2.82–2.58 (3H, m), 2.50 (2H, m), 2.20–1.75 (6H, m).

This was converted to the title compound (290 mg) by treating with oxalic acid in acetone according to the procedure for Example 1, mp: 230° C.

Example 8

1-[2-(2-Oxo-2,3-dihydro-benzooxazol-5-yl)ethyl]-piperidin-4-carboxylic acid (6-methoxy-[1,5]naphthyridin-4-yl)-amide, dioxalate

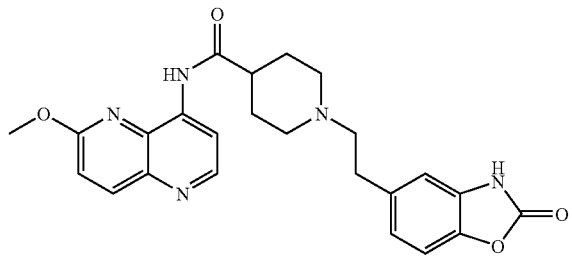

(a) (2-Oxo-2,3-dihydro-benzoxazol-5-yl)-acetic acid ethyl ester.

A mixture of (3-amino-4-hydroxy-phenyl)-acetic acid ethyl ester [RN86818-19-1](1.0 g, 5.12 mmol), urea (1.53 g, 25.5 mmol) and N,N-dimethylformamide (16 ml) was heated under reflux for 4 hours. The solvent was partly evaporated, the mixture was poured onto ice water and acidified with 1N hydrochloric acid. The precipitate was collected by filtration, washed with water and dried in vacuo to give the product (1.0 g, 75%).

δH(d-6 DMSO, 200 MHz): 11.35 (1H, br), 7.21 (1H, d), 7.01 (1H, s), 6.96 (1H, d), 4.08 (2H, q), 3.68 (2H, s), 1.18 (3H, t).

(b) 5-(2-Hydroxy-ethyl)-3H-benzoxazol-2-one.

Ester (a) (0.95 g, 4.29 mmol) was added portionwise to a cold solution (0° C.) of lithium aluminium hydride (0.206 g, 4.7 mmol) in tetrahydrofuran (20 ml). The mixture was then stirred 1.5 hours at room temperature and cooled again. The excess of hydride was hydrolysed by careful addition of water (0.2 ml), 5N aqueous sodium hydroxide solution (0.2 ml) and finally water (0.6 ml). Magnesium sulfate was added and the mixture was filtered. The filtrate was concentrated to dryness to give the product (0.5 g, 65%).

δH(d-6 DMSO, 200 MHz): 6.91 (1H, d), 6.78 (1H, s), 6.65 (1H, d), 6.56 (1H, s), 3.56 (2H, t), 2.66 (2H, t).

(c) Methanesulfonic acid 2-(2-oxo-2,3-dihydro-benzooxazol-5-yl)-ethyl ester.

Methanesulfonyl chloride (0.23 ml, 2.93 mmol) was added dropwise, at room temperature, to a solution of alcohol (b) (0.5 g, 2.79 mmol) and triethylamine (0.41 ml, 3 mmol) in tetrahydrofuran (20 ml) and the mixture was stirred for 3 hours. More methane sulfonyl chloride (0.1 ml) and triethylamine (0.1 ml) were added and stirring was continued over night. The same amount of reagent was added yet again and stirring continued for 2 hours. The solvent was then concentrated, the residue was suspended in water and extracted with dichloromethane. The organic phase was dried over magnesium sulfate and concentrated. The solid residue was chromatographed on silica gel eluting with heptane-ethyl acetate (1-1) to give the product (0.2 g, 28%).

δH(d-6 DMSO, 200 MHz): 7.22 (1H, d), 7.04 (1H, s), 7.00 (1H, d), 4.40 (2H, t), 3.12 (3H, s), 3.01 (2H, t).

(d) Title Compound.

A mixture of amine (1f) (0.234 g, 0.82 mmol), mesylate (c) (0.21 g, 0.82 mmol), potassium carbonate (0.124 g, 0.9 mmol) and acetonitrile (15 ml) was heated under reflux for 5 hours. The solvent was concentrated, the residue was suspended in water and extracted with dichloromethane. The organic phase was dried over magnesium sulfate and concentrated. The solid residue was chromatographed on silica gel eluting with dichloromethane-methanol (95-5) to give the free base of the title compound (29 mg, 8%).

δH(d-6 DMSO, 200 MHz): 9.75 (1H, br), 8.66 (1H, d), 8.40 (1H, d), 8.25 (1H, d), 7.29 (1H, d), 7.16 (1H, dd), 7.00–6.82 (2H, m), 4.12 (3H, s), 3.50 (1H, br), 3.00 (2H, m), 2.85–2.62 (3H, m), 2.50 (2H, m), 2.20–1.87 (4H, m), 1.74 (2H, m).

This was converted to the title compound (32 mg) by treating with oxalic acid in acetone according to the procedure for Example 1, mp: 180° C.

Example 9

1-(2-Quinoxalin-2-yl-ethyl)piperidine-4-carboxylic acid (6-methoxy-[1,5]naphthyridin-4-yl)-amide

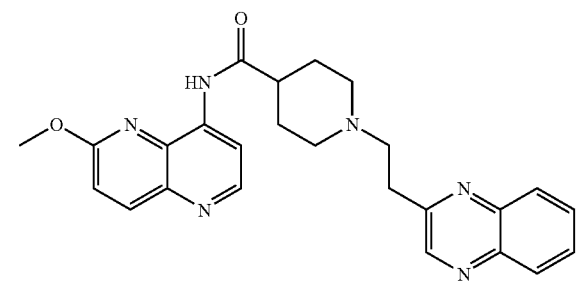

(a) Diethyl-(2-quinoxalin-2-yl-ethyl)-amine.

A solution of diethylamine hydrochloride (3.82 g, 35 mmol) and triethylamine (0.23 ml) in ethanol (1.75 ml) and water (1.75 ml) was added dropwise, at 60° C., to a mixture of 2-methyl-quinoxaline (5.0 g, 35 mmol), formaldehyde (2.81 g of 37% solution, 35 mmol), triethylamine (0.17 ml)

and ethanol (4.6 ml). The pH was adjusted to 7–7.5 by mean of dilute aqueous hydrochloric acid. Stirring was maintained 16 hours at 60° C. The solvent was concentrated, the residue was diluted with water and extracted with diethyl ether to remove the unreacted quinoxaline. The aqueous phase was basified with 20% aqueous sodium hydroxide (10 ml) and extracted with ethyl acetate. The organic phase was dried over magnesium sulfate and concentrated. The residue was chromatographed on silica gel eluting with dichloromethane-methanol (first 95-5 then 90-10 and finally 90-10 plus 0.1% of ammonia) to give diethyl-(2-quinoxalin-2-yl-ethyl)-amine (2.67 g, 37%).

δH(CDCl3, 200 MHz): 8.78 (1H, s), 8.05 (2H, m), 7.72 (2H, m), 3.17 (2H, m), 3.00 (2H, m), 2.64 (4H, q), 1.05 (6H, t).

(b) 2-Vinyl-quinoxaline.

Dimethyl sulfate (1.07 ml, 11.3 mmol) was added dropwise, while maintaining the mixture temperature below 40° C., to a solution of amine (a) (2.6 g 11.3 mmol) in ethanol (3 ml). The thick mixture was diluted with water (15 ml) then triethylamine (1.13 ml) was added and the mixture heated for 2 hours on a water bath. After cooling the mixture was extracted with diethyl ether. The organic phase was dried over magnesium sulfate, concentrated to dryness and the residue was chromatographed on silica eluting with heptane-ethyl acetate (3-1) to give the product (1.16 g, 66%).

δH(CDCl3, 200 MHz): 9.00 (1H, s), 8.07 (2H, m), 7.75 (2H, m), 7.05 (1H, dd), 6.48 (1H, dd), 5.80 (1H, dd).

(c) Title Compound.

A mixture of amine (1f) (0.403 g, 1.4 mmol), 2-vinyl-quinoxaline (b), (0.22 g, 1.4 mmol), acetic acid (0.1 ml) and ethanol (5.2 ml) was heated under reflux for 6 hours. The mixture was then made basic with aqueous sodium hydroxide and extracted with ethyl acetate. The organic phase was washed with water, dried over magnesium sulfate and concentrated. The residue was chromatographed on silica gel eluting with dichloromethane-methanol (99-1). After evaporation the residue was triturated with a small amount of ethyl acetate and crystallised. The solid was collected by filtration and dried to give the title compound (80 mg) mp.: 170° C.

δH(CDCl3, 200 MHz): 9.57 (1H, br), 8.79 (1H, s), 8.70 (1H, d), 8.51 (1H, d), 8.21 (1H, d), 8.15–7.98 (2H, m), 7.83–7.67 (2H, m), 7.15 (1H, d), 4.08 (3H, s), 3.35–3.06 (4H, m), 2.94 (2H, m), 2.48 (1H, tt), 2.48–1.80 (6H, m).

Example 10

1-[2-(1-Oxo-1,3,4,5-tetrahydro-benzo[c]azepin-2-yl)-ethyl]-piperidine-4-carboxylic acid (6-methoxy-[1,5]naphthyridin-4-yl)-amide oxalate

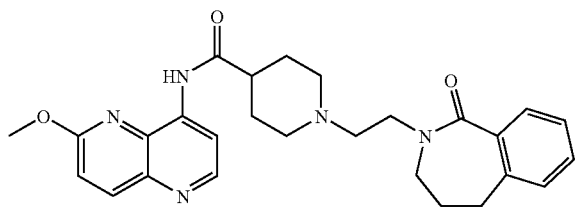

(a) 2-Allyl-2,3,4,5-tetrahydro-2-benzo(c)azepin-1-one

A solution of the 2,3,4,5-tetrahydro-2-benzo(c)azepin-1-one (prepared by ring expansion of 1-tetralone as described by Grunewald et al. J. Het. Chem., 1994, 3, 1612) (6.8 g, 42 mmol) in N,N-dimethylformamide (100 ml) was added dropwise to a stirred solution of 60% sodium hydride (2.02 g, 51 mmol) in N,N-dimethylformamide (50 ml) at 0° C. under argon. After stirrng for 1 hour, allyl bromide (3.9 ml, 46 mmol) in N,N-dimethylformamide (20 ml) was added, and the mixture stirred at room temperature for 1.5 hours. The crude reaction mixture was then poured onto water and extracted with ethyl acetate. The organic layer was dried and evaporated to afford the title compound (10 g).

MS (+ve ion electrospray) m/z 202 (MH+).

(b) (1-Oxo-1,3,4,5-tetrahydro-2-benzo(c)azepin-2-yl)-acetaldehyde

A solution of the olefin (a) (8 g, 40 mmol) in dichloromethane (500 ml) was cooled to −78° C., and ozone bubbled through the solution for 2.5 hours until the solution turned a blue/grey colour. Excess ozone was removed by purging with argon, triethylamine (10 ml) added dropwise, and then the solution was allowed to warm to room temperature. It was washed with dilute aqueous hydrochloric acid, followed by water and brine, then dried and evaporated to afford the crude product. Chromatography on silica eluting with 20% ethyl acetate/hexane afforded an oil (2.8 g).

MS (+ve ion electrospray) m/z 204 (MH+).

(c) Title Compound

A solution of amine (1f) (115 mg, 0.4 mmol), aldehyde (b) (90 mg, 0.44 mmol) in chloroform/methanol (2.3 ml/0.3 ml) was treated with freshly activated 3 Å molecular sieves and heated to reflux under argon for 8 hours. The cooled mixture was treated with sodium triacetoxyborohydride (130 mg, 0.6 mmol) and stirred for 16 hours at room temperature. The mixture was partitioned between ethyl acetate and saturated aqueous sodium bicarbonate solution. The organic extract was dried and evaporated to give a brown oil. Chromatography on silica eluting with a methanol/ethyl acetate gradient afforded the free base of the title compound as an oil (60 mg, 32%).

δH (CDCl3, 250 MHz), 9.60 (1H, bs), 8.70 (1H, d), 8.50 (1H, d), 8.20 (1H, d), 7.65 (1H, dd), 7.40–7.30 (2H, m), 7.20–7.10 (2H, m), 4.05 (3H, s), 3.75 (2H, t), 3.25 (2H, t), 3.10 (2H, m), 2.85 (2H, t), 2.70 (2H, t), 2.50 (1H, m), 2.30–1.90 (8H, m).

MS (+ve ion electrospray) m/z 474 (MH+).

This was converted into the oxalate (45 mg) by dissolving the oil in chloroform (4 ml) and adding an equivalent of oxalic acid in ether (6 ml). The resulting solid was isolated by centrifugation and dried in vacuo.

Example 11

1-[2-Oxo-2-(3-oxo-3,4dihydro-2H-benzo[1,4]thiazin-6-yl)-ethyl]-piperidine-4-carboxylic acid (6-methoxy-[1,5]naphthyridin-4-yl)-amide oxalate

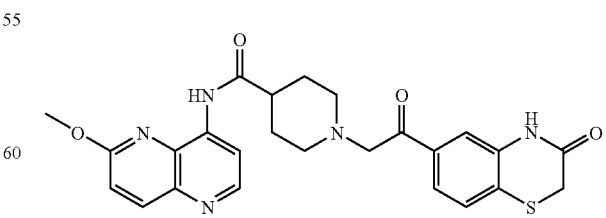

(a) 6-(2-Chloro-ethanoyl)-4H-benzo[1,4]thiazin-3-one

This was prepared by a modification of the procedure of Pesson and Techer (FR 1560628, 1969).

A solution of 3-oxo-3,4-dihydro-2H-benzo[1,4]thiazine (3 g, 18 mmol) and chloroacetyl chloride (1.6 ml) in 1,2-dichloroethane (10 ml) was treated portionwise with aluminium trichloride (5.3 g, 39.9 mmol), while maintaining the internal temperature below 10° C. with external cooling. After the addition was complete the mixture was heated to reflux for 1 hour, then allowed to recool to room temperature and added to a mixture of ice and concentrated aqueous hydrochloric acid (50 g/20 ml). The resulting precipitate was filtered, dried and recrystallised from boiling ethanol affording a yellow crystalline solid (1.87 g, 42%).

MS (+ve ion electrospray) m/z 243 (MH+).

(b) Title Compound

A mixture of piperidine (1f) (0.39 g) and potassium carbonate (0.2 g) in N,N-dimethylformamide (13 ml) was treated with (a) (0.33 g). After 7 hours the mixture was evaporated and the residue partitoned between ethyl acetate and saturated aqueous sodium bicarbonate solution. The organic extract was dried and evaporated to give a brown oil. Chromatography on silica eluting with a methanol/ethyl acetate gradient afforded the free base of the title compound as an oil (0.19 g).

δH(CDCl3, 200 MHz): 9.55 (1H, br), 8.72 (1H, d), 8.52 (1H, d), 8.20 (1H, d), 8.05 (1H, br), 7.70 (1H, d), 7.55 (1H, s), 7.40 (1H, d), 7.15 (1H, d), 4.10 (3H, s), 3.75 (2H, s), 3.45 (2H, s), 3.05 (2H, m), 2.40 (3H, m), 2.10 (4H, m).

MS (+ve ion electrospray) m/z 492 (MH+).

A portion of this material (20 mg) was converted to the title compound (20 mg) by treating with oxalic acid in ether according to a similar procedure as for Example 10.

Example 12

R,S-1-[2-Hydroxy-2-(3-oxo-3,4-dihydro-2H-benzo [1,4]thiazin-6-yl)-ethyl]-piperidine-4-carboxylic acid (6methoxy-[1,5]naphthyridin-4-yl)-amide oxalate

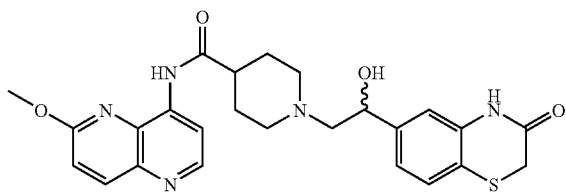

A mixture of Example 11 (0.15 g, 0.3 mmol) and chloroform/methanol/water (10 ml/50 ml/10 ml) was treated with sodium borohydride (18 mg) and stirred vigorously overnight. The mixture was evaporated and the residue partitioned between ethyl acetate and saturated aqueous sodium bicarbonate solution. The organic extract was dried and evaporated to give a brown oil. Chromatography on silica eluting with a methanol/dichloromethane gradient afforded the free base of the title compound as a solid (0.025 g).

δH(CDCl3, 200 MHz): 9.55 (1H, br), 8.70 (2H, m), 8.55 (1H, m), 8.25 (1H, d), 7.25 (1H, m), 7.15 (1H, d), 6.95 (2H, m), 4.72 (1H, dd), 4.10 (3H, s), 3.42 (2H, s), 2.95 (1H, m), 2.50 (4H, m), 2.20–1.90 (4H, m).

MS (+ve ion electrospray) m/z 494 (MH+).

This material (22 mg) was converted to the title compound (26 mg) by treating with oxalic acid in ether according to a similar procedure as for Example 10.

Example 13

1-[2-Oxo-2-(3-oxo-3,4-dihydro-2H-benzo[1,4]oxazin-6-yl)ethyl]-piperidine-4-carboxylic acid (6-methoxy-[1,5]naphthyridin-4-yl)-amide oxalate

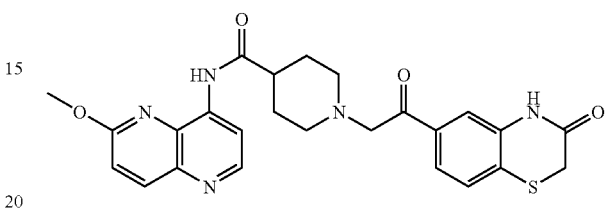

The free base of the title compound (61 mg) was prepared in 76% yield from piperidine (1f) and 6-(2-chloro-ethanoyl)-4H-benzo[1,4]oxazin-3-one by the same procedure as for Example 11(b).

δH(d6-DMSO, 200 MHz): 9.30 (1H, br), 8.70 (1H, d), 8.40 (1H, d), 8.25 (1H, d), 7.70 (1H, dd), 7.60 (1H, d), 7.35 (1H, d), 7.05 (1H, d), 4.70 (2H, m), 4.12 (3H, s), 3.75 (2H, s), 3.00 (2H, m), 2.80 (1H, m), 2.25 (2H, m), 1.95 (2H, m), 1.80 (2H, m).

MS (+ve ion electrospray) m/z 476 (MH+).

This material was converted to the title compound (65 mg) by treating with oxalic acid in ether according to a similar procedure as for Example 10.

Example 14

1-[2-(2,3-Dihydro-benzo[1,4]dioxin-6-yl)-2-oxoethyl]-piperidine-4-carboxylic acid (6methoxy-[1,5]naphthyridin-4-yl)-amide oxalate

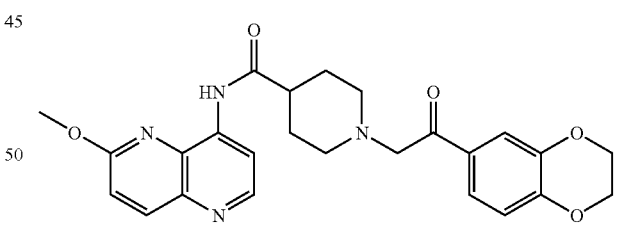

The free base of the title compound (0.21 g) was prepared from piperidine (1f) and 2-bromo-1-(2,3-dihydro-benzo[1,4]dioxin-6-yl)-ethanone in 43% yield according to the procedure of Example 11(b).

δH(CDCl3, 200 MHz): 9.58 (1H, br), 8.70 (1H, d), 8.50 (1H, d), 8.20 (1H, d), 7.60 (2H, m), 7.15 (1H, d), 6.90 (1H, d), 4.35–4.25 (4H, m), 4.10 (3H, s), 3.75 (2H, s), 3.10 (2H, m), 2.50 (1H, m), 2.35 (2H, m), 2.15–1.80 (6H, m).

MS (+ve ion electrospray) m/z 463 (MH+).

A portion of this material (20 mg) was converted to the title compound (25 mg) by treating with oxalic acid in ether according to a similar procedure as for Example 10.

Example 15

R and S-1-[2-Hydroxy-2-(2-oxo-2,3-dihydro-1H-pyrido[2,3-b][1,4]thiazin-7-yl)-ethyl]-piperidine-4-carboxylic acid (6-methoxy-[1,5]naphthyridin-4-yl)-amide hydrochloride

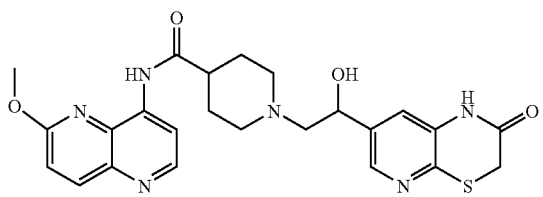

(a) 6-Methoxycarbonylmethylsulfanyl-5-nitro-nicotinic acid methyl ester

A solution of 6-chloro-5-nitro-nicotinic acid methyl ester (1.0 g) [prepared as described by A. H. Berrie et al. *J. Chem. Soc.* 2590–2594 (1951)] in dichloromethane (10 ml) containing triethylamine (0.76 ml) was treated with mercaptoacetic acid methyl ester (0.44 ml) and the solution was stirred at room temperature for 1 hour and evaporated to dryness. Sodium bicarbonate solution was added and the mixture was extracted with dichloromethane, dried (anhydrous sodium sulfate) and evaporated to afford a solid (1.0 g).

MS (+ve ion electrospray) m/z 287 (MH+).

(b) 2-Oxo-2,3-dihydro-1H-pyrido[2,3-b][1,4]thiazine-7-carboxylic acid methyl ester The ester (a) (1.0 g) in acetic acid (50 ml) was treated with iron powder (10 g) and the mixture was stirred and heated at 60° C. for 1 hour, cooled and filtered. The filtrate was evaporated, treated with sodium bicarbonate solution and extracted with warm chloroform. It was dried over sodium sulfate and evaporated to give a white solid (0.85 g).

MS (+ve ion electrospray) m/z 225 (MH+).

(c) 2-Oxo-2,3dihydro-1H-pyrido[2,3-b][1,4]thiazine-7-carboxylic acid

A solution of the ester (b) (2.8 g) in tetrahydrofuran (50 ml) was treated with 1M sodium hydroxide (30 ml). After 2 hours the mixture was concentrated to near dryness and acidified with 2M hydrochloric acid. Filtration and washing with water afforded a solid (2.5 g).

MS (−ve ion electrospray) m/z 209 (M-H⁻).

(d) 7-(2-Chloro-ethanoyl)-1H-pyrido[2,3-b][1,4]thiazin-2-one

A solution of acid (c) (1 g) in tetrahydrofuran (60 ml) was treated with triethylamine (0.7 ml) then at 0° C. with isobutylchloroformate (0.7 ml). After 0.5 hour the mixture was filtered and re-cooled to 0° C. A solution of excess diazomethane in ether was added, and the mixture stirred overnight at room temperature. Dichloromethane (20 ml) was added and the mixture was treated with 5M hydrochloric acid (10 ml). The mixture was stirred for 2 hours then partitioned between chloroform and saturated aqueous sodium bicarbonate solution. The organic extract was dried and evaporated affording an oil. Chromatography on silica eluting with an ethyl acetate/dichloromethane gradient afforded a solid (0.3 g) comprising a 3:2 mixture of the desired product together with methyl 2-oxo-2,3-dihydro-1H-pyrido[2,3-b][1,4]thiazine-7-carboxylate.

MS (+ve ion electrospray) m/z 243 MH+ of desired product)

(e) Title Compound

A solution of amine (1f) (123 mg) in N,N-dimethylformamide (2 ml) was treated with potassium carbonate (60 mg) and the product mixture (d) (0.2 g) at 0° C. After 3 hours water was added and the resulting precipitate was isolated by filtration. This material was suspended in methanol (70 ml) and treated with sodium borohydride (30 mg). After 2 hours the mixture was acidified with 2M hydrochloric acid and evaporated to dryness. The residue was partitioned between saturated aqueous sodium bicarbonate solution and chloroform. The organic extract was dried and evaporated. Chromatography on silica eluding with a 2–10% methanol in dichloromethane gradient afforded the free bases of the title compounds as a solid (0.14 g).

δH(CDCl3, 200 MHz): 9.55 (1H, br), 8.75 (1H, d), 8.55 (1H, d), 8.25 (1H, d) 8.15 (1H, d), 8.10 (1H, br), 7.25 (1H, d), 7.18 (1H, d), 4.80 (1H, dd), 4.15 (3H, s), 3.60 (2H, s), 3.25 (1H, m), 2.95 (1H, m), 2.60–2.40 (4H, m), 2.30–1.90 (5H, m).

MS (+ve ion electrospray) m/z 495 (MH+).

A portion of this racemic material (80 mg) was subject to preparative hplc on a Chiralcell OD column (10 micron particle size) eluting with hexane/ethanol/50% aqueous hydroxylamine in a 50/50/0.1 v/v/v ratio. The sample was separated in 20×4 mg runs. The faster stereoisomer had a retention time of 13.8 minutes, the slower a retention time of 22.6 minutes. Around 30 mg of each stereoisomer were eventually isolated and each isomer had an enantiomeric excess of >92%.

Each sample was dissolved in methanol/chloroform (3 ml/3 ml) and treated with a 1M solution of hydrochloric acid in ether (2 ml) then diluted with ether (5 ml). The resultant precipitates were isolated by centrifugation and dried in vacuo affording the title compounds (each ca 30 mg).

Example 16

1-[2-(2,3-Dihydro-[1,4]dioxino[2,3-c]pyridin-7-yl)-ethyl]-piperidine-4-carboxylic acid (6-methoxy-[1,5]naphthyridin-4-yl)-amide hydrochloride

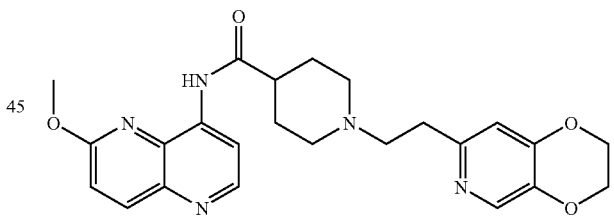

(a) 5-Benzyloxy-2-hydroxymethyl-1H-pyridin-4-one

A mixture of 5-benzyloxy-2-hydroxymethyl-4-pyrone (prepared from Kojic acid by the method of D. Erol, J. Med. Chem., 1994, 29, 893) (9.7 g, 40 mmol), concentrated aqueous (880) ammonia (100 ml), and ethanol (20 ml) was heated to reflux overnight. The mixture was allowed to cool to room temperature then filtered. The resultant solid was washed with ether and dried in vacuo (5.9 g).

MS (+ve ion electrospray) m/z 232 (MH+).

(b) (2,3-Dihydro-[1,4]dioxino[2,3-c]pyridin-7-yl)-methanol

A solution of (a) (2 g, 8.7 mmol) in water (220 ml) containing sodium hydroxide (17 mmol) was hydrogenated over 10% palladium on charcoal (1g) for 4 hours. The mixture was filtered and evaporated to give a white solid. This solid was dissolved in N,N-dimethylformamide (8 ml) then treated with potassium carbonate (2.9 g) and 1,2-dibromoethane (0.6 ml, 7 mmol). The mixture was heated at 85° C. overnight. The cooled mixture was evaporated onto silica and chromatographed eluting with 10–30% methanol in ethyl acetate affording a white solid (250 mg, 21%).

MS (+ve ion electrospray) m/z 232 (MH+).

(c) 2,3-Dihydro-[1,4]dioxino[2,3-c]pyridine-7-carboxaldehyde

A solution of (b) (250 mg, 1.5 mmol) in dichloromethane (5 ml) was treated with manganese dioxide (650 mg, 7.5 mmol). After 3 days the mixture was filtered and evaporated affording a white solid (150 mg, 61%).

MS (+ve ion electrospray) m/z 166 (MH+).

(d) 1-(2,3-Dihydro-[1,4]dioxino[2,3-c]pyridin-7-yl)-2-trimethylsilanyl-ethanol

A solution of aldehyde (c) (1.2 g) in tetrahydrofuran (20 ml) was treated at 0° C. under argon with a solution of trimethylsilylmethylmagnesium chloride in ether (1M; 8 ml, 8 mmol). After 2 hours the mixture was partitioned between ether—half saturated aqueous ammonium chloride solution. The organic extract was dried and evaporated affording an oil (1.6 g).

MS (+ve ion electrospray) m/z 254 (MH+).

(e) 7-Vinyl-2,3-dihydro-[1,4]dioxino[2,3-c]pyridine

A solution of (d) (1.6 g) in tetrahydrofuran (20 ml) was treated at 0° C. under argon with a solution of potassium t-butoxide in tetrahydrofuran (1M; 7.6 ml, 7.6 mmol). After 2 hours the mixture was partitioned between ethyl acetate—half saturated aqueous ammonium chloride solution. The organic extract was dried and evaporated affording an oil (1.5 g).

MS (+ve ion electrospray) m/z 164 (MH+).

(f) Title Compound

A mixture of olefin (e) (65 mg) and amine (1f) (115 mg) in ethanol (1 ml) containing acetic acid (25 mg) was heated to reflux for 3 days. The mixture was partitioned between ethyl acetate and 1M sodium hydroxide solution. The organic extract was dried and evaporated affording an oil (0.2 g). Chromatography on silica eluting with a 0–20% methanol in ethyl acetate gradient afforded the free base of the title compound as a solid (36 mg).

δH(CD$_3$OD, 200 MHz): 8.62 (1H, d), 8.50 (1H, d), 8.20 (1H, d), 8.00 (1H, s), 7.25 (1H, d), 6.88 (1H, s), 4.36 (2H, m), 4.30 (2H, m), 4.15 (3H, s), 2.82 (1H, m), 2.55 (2H, m), 2.20–2.00 (4H, m), 1.45–1.25 (4H, m), 1.90 (2H, m).

MS (+ve ion electrospray) m/z 450 (MH+).

This was converted to the hydrochloride salt (42 mg) by the method of Example 15.

Example 17

R,S-6-{1-Hydroxy-2-[4-(6methoxy-[1,5]naphthyridin-4-yloxymethyl)-piperidin-1-yl]-ethyl}-4H-benzo[1,4]thiazin-3-one hydrochloride

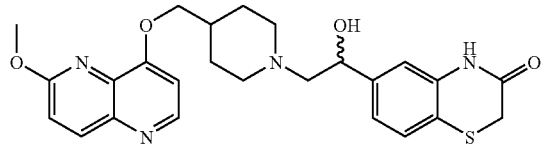

(a) 4-(6-Methoxy-[1,5]naphthyridin-4-yloxymethyl)-piperidine-1-carboxylic acid tert-butyl ester 4-Hydroxymethyl-piperidine-1-carboxylic acid tert-butyl ester (610 mg) was added to a stirred suspension of sodium hydride (120 mg of a 60% dispersion in mineral oil) in N,N-dimethylformamide (6 ml) at 0° C. under argon. After 1 hour triflate (1b) (924 mg) was added and the mixture was heated at 95° C. overnight. The mixture was partitioned between ethyl acetate and water. The organic extract was washed with brine then dried and evaporated affording an oil (1 g). Chromatography on silica eluting with a 0–100% ethyl acetate in dichloromethane gradient afforded an oil (0.54 g, 48%).

MS (+ve ion electrospray) m/z 374 MH+).

(b) 2-Methoxy-8-(piperidin-4-ylmethoxy)-[1,5]naphthyridine

A solution of carbamate (a) (0.95 g) in dichloromethane/trifluoroacetic acid (20 ml/20 ml) was stirred for 1 hour then evaporated to dryness, azeotroping with toluene and chloroform. The residue was dissolved in water and extracted with ethyl acetate. The aqueous extract was basified with solid potassium carbonate and evaporated. The residue stirred with 10% methanol in chloroform. Filtration and evaporation afforded an oil (0.7 g).

MS (+ve ion electrospray) m/z 274 (MH+).

(c) 6-{2-[4-(6-Methoxy-[1,5]naphthyridin-4-yloxymethyl)-piperidin-1-yl]-ethanoyl}-4H-benzo[1,4]thiazin-3-one A solution of amine (b) (0.4 g) in N,N-dimethylformamide (5 ml) was treated with potassium carbonate (0.3 g) then chloromethylketone (11a) (0.36 g). The mixture was stirred overnight then filtered and concentrated to around 2 ml of N,N-dimethylformamide. Water (ca 5 ml) was added dropwise, and the resulting yellow solid was isolated by filtration and dried in vacuo (0.5 g, 73%).

MS (+ve ion electrospray) m/z 479 (MH+).

(d) Title Compound

A solution of ketone (c) (0.5 g) in methanol/chloroform (180 ml/22 ml) was treated with sodium borohydride (0.15 g). After 1 hour the mixture was acidified with 5M hydrochloric acid then basified with saturated aqueous sodium bicarbonate solution. The mixture was concentrated then extracted with ethyl acetate. The organic extract was washed with brine then dried and evaporated affording an oil. Chromatography on silica eluting with a 0–5% methanol in ethyl acetate gradient afforded a white solid (0.3 g, 63%).

δH(CDCl3, 200 MHz): 9.85 (1H, br), 8.60 (1H, d), 8.18 (1H, d), 7.28 (1H, m), 7.12 (1H, d), 7.02–6.95 (2H, m), 6.90 (1H, d), 4.70 (1H, dd), 4.10 (5H, m), 3.40 (2H, s), 3.25 (1H, m), 2.90 (1H, m), 2.50 (1H, m), 2.40 (2H, m), 2.20–2.00 (4H, m), 1.60 (2H, m).

MS (+ve ion electrospray) m/z 481 (MH+).

This was converted to the hydrochloride salt by the procedure of Example 15.

Example 18

R,S-1-[2-(2,3-Dihydro-benzo[1,4]dioxin-6-yl)-2-hydroxy-ethyl]-piperidine-4-carboxylic acid (6-methoxy-[1,5]naphthyridin-4-yl)-amide oxalate

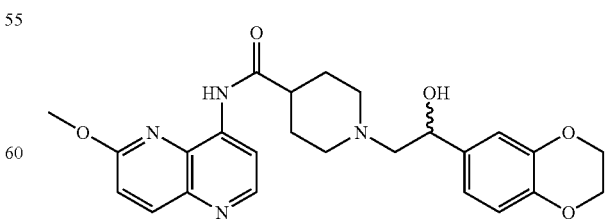

This was prepared from Example 14 by reduction with sodium borohydride by the method of Example (17d).

δH(CDCl3, 200 MHz): 9.60 (1H, br), 8.70 (1H, d), 8.52 (1H, d), 8.25 (1H, d), 7.20 (1H, d), 6.90–6.80 (3H, m), 4.70

(1H, dd), 4.25 (4H, s), 4.10 (3H, s), 3.30 (1H, m), 3.00 (1H, m), 2.60–2.40 (5H, m), 2.30–1.90 (4H, m).

MS (+ve ion electrospray) m/z 481 (MH+).

This was converted to the oxalate salt (10 mg) by the procedure of Example 15.

Example 19

R,S-1-[2-Hydroxy-2-(3-oxo-3,4-dihydro-2H-benzo[1,4]oxazin-6-yl)-ethyl]-piperidine-4-carboxylic acid (6-methoxy-[1,5]naphthyridin-4-yl)-amide oxalate

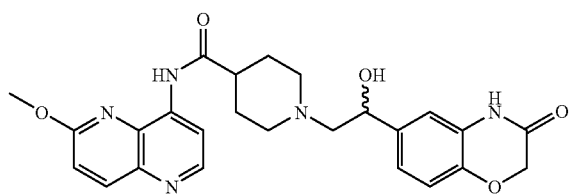

The free base of the title compound was prepared from Example 13 by reduction with sodium borohydride by the method of Example (17d) but the reaction was for 1 hour and without chloroform as the co-solvent.

δH(d-6 DMSO, 200 MHz): 9.77 (1H, br), 8.68 (1H, d), 8.40 (1H, d), 8.30 (1H, d), 7.30 (1H, d), 6.95–6.88 (3H, m), 5.00 (1H, br), 4.66 (1H, m), 4.55 (2H, s), 4.15 (3H, s), 3.00 (2H, m), 2.70 (1H, m), 2.50–2.35 (2H, m), 2.20–2.10 (2H, m), 2.00–1.90 (2H, m), 1.85–1.65 (2H, m).

MS (+ve ion electrospray) m/z 478 (MH+).

This material was converted to the title compound (44 mg) by treating with oxalic acid in ether according to a similar procedure as for Example 10.

Example 20

1-[2-(4-Fluoro-1H-benzoimidazol-2-yl)ethyl]-piperidine-4-carboxylic acid [6-(3-amino-propoxy)-[1,5]naphthyridin-4-yl]-amide bis-trifluoroacetate

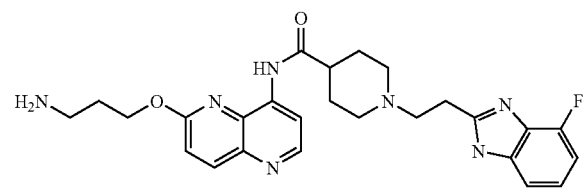

(a) 8-Aminol-H-[1,5]naphthyridin-2-one hydrobromide

A suspension of amine (1c) (4.20 g, 24 mmol) in concentrated hydrobromic acid (35 ml) was heated at 120° C. for 2 hours. The mixture was set aside in the refrigerator for 2 hours, then filtered, washing with small amounts of cold water then diethyl ether. Drying in vacuo afforded the product as a white solid (6.1 g, 100%).

MS (+ve ion electrospray) m/z 162 (MH+).

(b) [3-(8-Amino-[1,5]naphthyridin-2-yloxy)-propyl]-carbamic acid tert-butyl ester A suspension of hydrobromide salt (a) (1.2 g, 5 mmol) in N,N-dimethylformamide (10 ml) at 40° C. was treated with potassium carbonate (2.1 g, 15 mmol) then after 0.25 hours with a solution of (3-bromo-propyl)-carbamic acid tert-butyl ester (2 g, 7.4 mmol) in N,N-dimethylformamide (5 ml). The mixture was heated for 4 hours at 40° C., then evaporated to dryness. The residue was partitioned between ethyl acetate and dilute aqueous sodium chloride solution. The organic extract was dried and evaporated to give a brown oil (2.2 g) This was chromatographed on silica eluting with a methanol/ethyl acetate gradient affording the product as a clear oil (1.0 g).

MS (+ve ion electrospray) m/z 319 (MH+).

(c) (3-{8-[(1-{1-[2-(4-Fluoro-1H-benzoimidazol-2-yl)-ethyl]-piperidin-4-yl}-methanoyl)-amino]-[1,5]naphthyridin-2-yloxy}-propyl)-carbamic acid tert-butyl ester This was prepared from amine (b) and acid (4c) in 42% yield according to the procedure for Example (4d) affording an oil (0.31 g).

MS (+ve ion electrospray) m/z 592 (MH+).

(d) Title Compound

The carbamate (c) (0.20 g) was treated with trifluoroacetic acid (20 ml). After 2 hours the mixture was evaporated and the residue triturated with chloroform, affording the title compound as a white solid (0.13 g).

δH(d-6 DMSO, 200 MHz): 10.00 (1H, br), 8.80 (1H, d), 8.50 (1H, d), 8.35 (1H, d), 7.80 (3H, br), 7.15 (1H, m), 7.00 (1H, m), 4.70 (2H, t), 3.90–2.90 (1H, m), 2.20–1.80 (6H, m).

MS (+ve ion electrospray) m/z 492 (MH+).

Example 21

8-{1-[2-(2,3-Dihydro-benzo[1,4]dioxin-6-yl)-ethyl]-piperidin-4-ylmethoxy}-2-methoxy-[1,5]naphthyridine hydrochloride

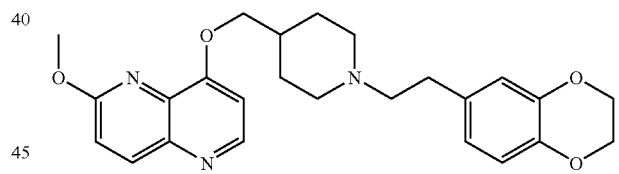

(a) 6-(2-Chloro-ethyl)-2,3-dihydro-benzo[1,4]dioxine

A solution of 2-chloro-1-(2,3-dihydro-benzo[1,4]dioxin-6-yl)-ethanone (0.5 g) in trifluoroacetic acid/triethylsilane (4 ml/1.3 ml) was stirred overnight then partitioned between dichloromethane and dilute aqueous sodium bicarbonate solution. The organic extract was dried and evaporated to give a brown oil (0.42 g) This was chromatographed on silica eluting with a dichloromethane/petroleum ether gradient affording the product as a clear oil (0.23 g).

MS (+ve ion electrospray) m/z 199 (MH+).

(b) 6-(2-Iodo-ethyl)-2,3-dihydro-benzo[1,4]dioxine

A solution of (a) (0.22 g) in acetone (10 ml) was treated with sodium iodide (0.6 g) and heated to reflux overnight. The mixture was filtered and evaporated. The residue was partitioned between dichloromethane and dilute aqueous sodium sulphite solution. The organic extract was dried and evaporated to give a brown oil (0.25 g).

MS (+ve ion electrospray) m/z 291 (MH+).

(c) Title Compound

This was prepared from Example (17b) (0.17 g) and Example (21b) (0.2 g) following the procedure for Example (1j) affording after chromatography the free base of the title compound as an oil (0.12 g).

δH(CD₃OD, 200 MHz): 8.50 (1H, d), 8.10 (1H, d), 7.20 (1H, d), 7.15 (1H, d), 6.75–6.60 (3H, m), 4.20 (4H, s), 4.15 (1H, d), 4.07 (3H, s), 3.10 (2H, m), 2.70 (2H, m), 2.55 (2H, m), 2.15 (2H, m), 2.00 (2H, m), 1.45 (2H, m).

MS (+ve ion electrospray) m/z 436 (MH+).

This was converted to the hydrochloride salt (0.13 g) by the procedure of Example 15.

The following compounds were prepared by procedures analogous to those described herein:

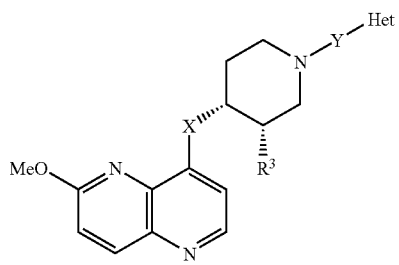

| Example | Name | X | R³ | Y | Het | Preparation |
|---------|------|---|----|----|-----|-------------|
| 22 | 6-{2-[4-(6-Methoxy-[1,5]naphthyridin-4-yloxymethyl)-piperidin-1-yl]-ethyl}-4H-benzo[1,4]thiazin-3-one | OCH₂ | H | CH₂CH₂ | (benzothiazinone) | Alkylation of amine (17b) with (1i) according to the procedure of Example (1j). |
| 23 | [(3R,4S)-4-[(6-Methoxy-[1,5]naphthyridin-4-ylcarbamoyl)-methyl]-1-(3-oxo-3,4-dihydro-2H-benzo[1,4]thiazin-6-ylmethyl)-piperidin-3-yl]-acetic acid trifloroacetate salt | NHCOCH₂ | CH₂CO₂H | CH₂ | (benzothiazinone) | Reaction of (3R,4S)-3-tert-butoxycarbonylmethyl-4-carboxymethyl-piperidine-1-carboxylic acid benzyl ester (prepared from ((3R,4S)-3-vinyl-piperidin-4-yl)-acetic acid methyl ester by methods described in WO 00343383) with (1c) by the method of Example (1e) followed by hydrogenation (Pd/C) and reaction with 3-oxo-3,4-dihydro-2H-benzo[1,4]thiazine-6-carbaldehyde and triacetoxyborohydride, followed by deprotection with TFA. |

Biological Activity

The MIC (μg/ml) of test compounds against various organisms was determined: *S. aureus* Oxford, *S. aureus* WCUH29, *S. pneumoniae* 1629, *S. pneumoniae* N1387, *S. pneumoniae* ERY 2, *E. faecalis* I, *E. faecalis* 7,*H. influenzae*Q1, *H. influenzae* NEMC1, *M. catarrhalis* 1502.

Examples 1–4, 12, 13, 15, 16, 18 had MIC values ≦4 μg/ml versus all these organisms.

Examples 7, 14, 17, 19, 22 had MIC values ≦16 μg/ml versus all these organisms.

Examples 5,6, 9,11, 21, 22 had MIC values ≦64 μg/ml versus all these organisms.

Other examples had MIC values less than 64 μg/ml versus at least one of these organisms.

What is claimed is:

1. A compound of formula (I) or a pharmaceutically acceptable salt, solvate and/or N-oxide thereof:

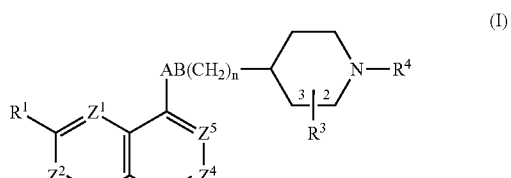

wherein:

one of $Z^1$, $Z^2$, and $Z^3$ is N, one of the remainder of $Z^1$, $Z^2$, $Z^3$, $Z^4$, and $Z^5$ is $CR^{1a}$ and the remainder are CH;

$R^1$ and $R^{1a}$ are independently selected from hydrogen; hydroxy; $(C_{1-6})$ alkoxy optionally substituted by $(C_{1-6})$alkoxy, amino, piperidyl, guanidino or amidino any of which is optionally N-substituted by one or two $(C_{1-6})$alkyl, acyl or $(C_{1-6})$alkylsulphonyl groups, CONH2, hydroxy, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$alkoxy-substituted $(C_{1-6})$alkyl; halogen; $(C_{1-6})$alkyl; $(C_{1-6})$alkylthio; trifluromethyl; nitro; azido; acyl; acyloxy; acylthio; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups, or when $Z^1$ is $CR^{1a}$, $R^1$ and $R^{1a}$ may together represent $(C_{1-2})$alkylenedioxy, or when $Z^5$ is $CR^{1a}$, $R^{1a}$ may instead be cyano, hydroxymethyl or carboxy, provided that when $Z^1$, $Z^2$, $Z^3$, $Z^4$ and $Z^5$ are $CR^{1a}$ or CH, then $R^1$ is not hydrogen;

$R^3$ is hydrogen; or $R^3$ is in the 2- or 3-position and is:

carboxy; $(C_{1-6})$alkoxycarbonyl; aminocarbonyl wherein the amino group is optionally substituted by hydroxy, $(C_{1-6})$alkyl, hydroxy$(C_{1-6})$alkyl, aminocarbonyl$(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy $(C_{1-6})$alkyl, aminocarbonyl$(C_{1-6})$alkyl or $(C_{2-6})$alkenyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; or $(C_{1-4})$alkyl or ethenyl optionally substituted with any of the groups listed above for $R^3$ and/or 0 to 2 groups $R^{12}$ independently selected from:

halogen; $(C_{1-6})$alkylthio; trifluoromethyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$alkyl, hydroxy$(C_{1-6})$alkyl, aminocarbonyl$(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; oxo; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl; or when $R^3$ is in the 3-position it may instead be selected from hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl, and amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl;

in addition when $R^3$ is disubstituted with a hydroxy or amino containing substituent and a carboxy containing substituent these may optionally together form a cyclic ester or amide linkage, respectively;

$R^{10}$ is selected from $(C_{1-4})$alkyl; $(C_{2-4})$alkenyl and aryl any of which may be optionally substituted by a group $R^{12}$ as defined above; carboxy; aminocarbonyl wherein the amino group is optionally substituted by hydroxy, $(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl or $(C_{2-6})$alkenyl; $(C_{1-6})$alkylsulphonyl; trifluoromethylsulphonyl; $(C_{2-6})$alkenylsulphonyl; $(C_{1-6})$alkoxycarbonyl; $(C_{1-6})$alkylcarbonyl; $(C_{2-6})$alkenyloxycarbonyl; and $(C_{2-6})$alkenylcarbonyl;

$R^4$ is a group —U—V—$R^5$ where $R^5$ is an optionally substituted bicyclic carbocyclic or heterocyclic ring system (A):

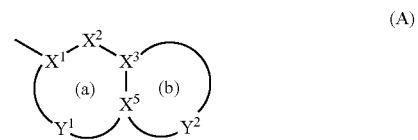

containing up to four heteroatoms in each ring in which at least one of rings (a) and (b) is aromatic;

$X^1$ is C or N when part of an aromatic ring or $CR^{14}$ or N when part of a non aromatic ring;

$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;

$X^3$ and $X^5$ are independently N or C;

$Y^1$ is a 0 to 4 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring, $y^2$ is a 2 to 6 atom linker group, each atom of $Y^2$ being independently selected from N, $NR^{13}$, O, $S(O)_x$, CO and $CR^{14}$ when part of an aromatic or non-aromatic ring or may additionally be $CR^{14}R^{15}$ when part of a non aromatic ring;

each of $R^{14}$ and $R^{15}$ is independently selected from: H; $(C_{1-4})$alkylthio; halo; carboxy$(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy$(C_{1-4})$alkyl; mercapto$(C_{1-4})$alkyl; $(C_{1-4})$alkoxy; nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; aryl; aryl$(C_{1-4})$alkyl; aryl$(C_{1-4})$alkoxy each $R^{13}$ is independently hydrogen, trifluoromethyl; $(C_{1-4})$alkyl optionally substituted by hydroxy, carboxy, $(C_{1-6})$alkoxycarbonyl, $(C_{1-6})$alkoxy, $(C_{1-6})$alkylthio, halo or trifluoromethyl; $(C_{2-4})$alkenyl; aryl; aryl $(C_{1-4})$alkyl; arylcarbonyl; heteroarylcarbonyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$ alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl;

each x is independently 0, 1 or 2;

U is CO, $SO_2$ or $CH_2$ and V is $CR^{17}R^{18}$ or U is $CH_2$ and V is CO, $SO_2$ or $CR^{17}R^{18}$;

$R^{17}$ and $R^{18}$ are independently selected from hydrogen, hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; and amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl;

n is 0 or 1 and AB is $NR^{11}CO$, $CONR^{11}$, $CO-CR^8R^9$, $CR^6R^7CO$, $O-CR^8R^9$, $CR^6R^7-O$, $NR^{11}-CR^8R^9$, $CR^6R^7-NR^{11}$, $NR^{11}SO_2$, $CR^6R^7-SO_2$ or $CR^6R^7CR^8R^9$;

or n is 0 or 1 and AB is NH—CO—NH or NH—CO—O;

or n is 0 and AB is $CR^6R^7SO_2NR^{11}$, $CR^6R^7CONR^{11}$ or $CR^6R^7CH_2NR^{11}$;

provided that $R^6$ and $R^7$, and $R^8$ and $R^9$ are not both optionally substituted hydroxy or amino;

and wherein:

each of $R^6$, $R^7$, $R^8$ and $R^9$ is independently selected from: H; $(C_{1-6})$alkoxy; $(C_{1-6})$alkylthio; halo; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy, amino or aminocarbonyl optionally substituted as for corresponding substituents in $R^3$; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl;

or $R^6$ and $R^8$ together represent a bond and $R^7$ and $R^9$ are as above defined;

and each $R^{11}$ is independently H; trifluoromethyl; $(C_{1-6})$alkyl; $(C_{2-6})$alkenyl; $(C_{1-6})$alkoxycarbonyl; $(C_{1-6})$alkylcarbonyl; or aminocarbonyl wherein the amino group is optionally substituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl or $(C_{2-6})$alkenyl and optionally further substituted by $(C_{1-6})$alkyl or $(C_{2-6})$alkenyl;

or where one of $R^3$ and $R^6$, $R^7$, $R^8$ or $R^9$ contains a carboxy group and the other contains a hydroxy or amino group they may together form a cyclic ester or amide linkage.

2. A compound according to claim 1 wherein $Z^1$ is N, $Z^3$ is CH or CF and $Z^2$, $Z^4$ and $Z^5$ are each CH.

3. A compound according to claim 1 wherein $R^1$ is methoxy and $R^{1a}$ is H or when $Z^3$ is $CR^{1a}$ it may be C—F.

4. A compound according to claim 1 wherein $R^3$ is hydrogen or hydroxy.

5. A compound according to claim 1 wherein n is 0 and either A is CHOH or $CH_2$ and B is $CH_2$ or A is NH and B is CO.

6. A compound according to claim 1 wherein the group —U—V— is —$(CH_2)_2$—, $CH_2CH(OH)$ or $CH_2CO$.

7. A compound according to claim 1 wherein the heterocyclic ring (A) has ring (a) aromatic selected from optionally substituted benzo and pyrido and ring (b) non-aromatic in which preferably $Y^2$ has 3–5 atoms including $NR^{13}$, where $R^{13}$ is other than hydrogen, O or S bonded to $X^5$ and NHCO bonded via N to $X^3$, or O bonded to $X^3$; or ring (a) is aromatic and (b) is aromatic.

8. A compound according to claim 1 wherein $R^5$ is selected from:
4H-benzo[1,4]thiazin-3-one-6-yl;
benzo[1,3]dioxol-5-yl;
2,3-Dihydro-benzo[1,4]dioxin-6-yl;
4-fluorobenzimidazol-2-yl;
benzo[1,2,5]thiadiazol-5-yl;
quinoxalin-2-yl;
2-oxo-2,3-dihydro-1H-pyrido[2,3-b][1,4]thiazin-7-yl; and
2,3-dihydro-[1,4]dioxino[2,3-c]pyridin-7-yl.

9. A compound selected from:
1-[2-(3-Oxo-3,4-dihydro-2H-benzo[1,4]thiazin-6-yl)-ethyl]-piperidine-4-carboxylic acid (6-methoxy-[1,5]naphthyridin-4-yl)-amide;
1-(2-Benzo[1,3]dioxol-5-yl-ethyl)-piperidine-4-carboxylic acid (6-methoxy-[1,5]naphthyridin-4-yl)-amide;
1-[2-(2,3-Dihydro-benzo[1,4]dioxin-6-yl)-ethyl]-piperidine-4-carboxylic acid (6-methoxy-[1,5]naphthyridin-4-yl)-amide;
1-[2-(4-Fluoro-1H-benzoimidazol-2-yl)-ethyl]-piperidine-4-carboxylic acid (6-methoxy-[1,5]naphthyridin-4-yl)-amide;
1-(2-Benzo1,2,5thiadiazol-5-yl-ethyl)-piperidine-4-carboxylic acid (6-methoxy-[1,5]naphthyridin-4-yl)-amide;
1-[2-(3-Methyl-2-oxo-2,3-dihydro-benzooxazol-6-yl)-ethyl]-piperidine-4-carboxylic acid (6-methoxy-[1,5]naphthyridin-4-yl)-amide;
1-[2-(3-Oxo-3,4-dihydro-2H-benzo[1,4]oxazin-6-yl)-ethyl]-piperidine-4-carboxylic acid (6-methoxy-[1,5]naphthyridin-4-yl)-amide;
1-[2-(2-Oxo-2,3-dihydro-benzooxazol-5-yl)-etheyl]-piperidine-4-carboxylic acid (6-methoxy-[1,5]naphthyridin-4-yl)-amide;
1-(2-Quinoxalin-2-yl-ethyl)-piperidine-4-carboxyl acid (6-methoxy-[1,5]naphthyridin-4-yl)-amide;
1-[2-(1-Oxo-1,3,4,5-tetrahydro-benzo[c]azepin-2-yl)-ethyl]-piperidine-4-carboxylic acid (6-methoxy-[1,5]naphthyridin-4-yl)-amide;
1-[2-Oxo-2-(3-oxo-3,4-dihydro-2H-benzo[1,4]thiazin-6-yl)-ethyl]-piperidine-4-carboxylic acid (6-methoxy-[1,5]naphthyridin-4-yl)-amide;
R,S-1-[2-Hydroxy-2-(3-oxo-3,4-dihydro-2H-benzo[1,4]thiazin-6-yl)-ethyl]-piperidine-4-carboxylic acid (6-methoxy-[1,5]naphthyridin-4-yl)-amide;
1-[2-Oxo-2-(3-oxo-3,4-dihydro-2H-benzo[1,4]oxazin-6-yl)-ethyl]-piperidine-4-carboxylic acid (6-methoxy-[1,5]naphthyridin-4-yl)-amide;
1-[2-(2,3-Dihydro-benzol[1,4]dioxin-6-yl)-2-oxo-ethyl]-piperidine-4-carboxylic acid (6-methoxy-[1,5]naphthyridin-4-yl)-amide;
R and S-1-[2-Hydroxy-2-(2-oxo-2,3-dihydro-1H-pyrido[2,3-b][1,4]thiazin-7-yl)-ethyl]-piperidine-4-carboxylic acid (6-methoxy-[1,5]naphthyridin-4-yl)-amide;
1-[2-(2,3-Dihydro-[1,4]dioxino[2,3-c]pyridin-7-yl)-ethyl]-piperidine-4-carboxylic acid (6-methoxy-[1,5]naphthyridin-4-yl)-amides;
R,S-6-{1-Hydroxy-2-[4-(6-methoxy-[1,5]naphthyridin-4-yloxymethyl)-piperidin-1-yl]-ethyl}-4H-benzo[1,4]thiazin-3-one;

R,S-1-[2-(2,3-Dihydro-benzo[1,4]dioxin-6-yl)-2-hydroxy-ethyl]-piperidine-4-carboxylic acid (6-methoxy-[1,5]naphthyridin-4-yl)-amide;

R,S-1-[2-Hydroxy-2-(3-oxo-3,4-dihydro-2H-benzo[1,4]oxazin-6-yl)-ethyl]-piperidine-4-carboxylic acid (6-methoxy-[1,5]naphthyridin-4-yl)-amide;

1-[2-(4-Fluoro-1H-benzoimidazol-2-yl)-ethyl]-piperidine-4-carboxylic acid [6-(3-amino-propoxy)-[1,5]naphthyridin-4-yl]-amide;

8-{1-[2-(2,3-Dihydro-benzo[1,4]dioxin-6-yl)-ethyl]-piperidin-4-ylmethoxy}-2-methoxy-[1,5]naphthyridine;

6-{2-[4-(6-Methoxy-[1,5]naphthyridin-4-yloxymethyl)-piperidin-1-yl]-ethyl}-4H-benzo [1,4]thiazin-3-one; and

[(3R,4S)-4-[(6-Methoxy-[1,5]naphthyridin-4-ylcarbamoyl)-methyl]-1-(3-oxo-3,4-dihydro-2H-benzo[1,4]thiazin-6-ylmethyl)-piperidin-3-yl]-acetic acid;

or a pharmaceutically acceptable salt, solvate and/or N-oxide thereof.

10. A compound according to claim 7, wherein $Y^2$ contains 2–3 heteroatoms, one of which is S and 1–2 are N, with one N bonded to $X^3$.

11. A method of treatment of bacterial infections in mammals, which method comprises the administration to a mammal in need of such treatment an effective amount of a compound according to claim 1.

12. A method according to claim 11, wherein said mammal is man.

13. A pharmaceutical composition comprising a compound according to claim 1, and a pharmaceutically acceptable carrier.

14. A process for preparing a compound according to claim 1, which process comprises reacting a compound of formula (IV) with a compound of formula (V):

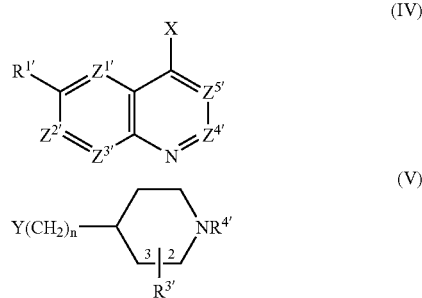

wherein n is as defined in formula (I); $Z^{1'}$, $Z^{2'}$, $Z^{3'}$, $Z^{4'}$ and $Z^{5'}$ are $Z^1$, $Z^2$, $Z^3$, $Z^4$ and $Z^5$ as defined in formula (I) or one of $Z^1$, $Z^2$, $Z^3$, $Z^4$, $Z^5$ is $CR^{1a'}$ and $R^{1a'}$, $R^{1'}$, $R^{3'}$ and $R^{4'}$ are $R^{1a}$, $R^1$, $R^3$ and $R^4$ optionally containing hydroxy or N protecting groups or $R^{4'}$ is H or an N-protecting group;

and X and Y may be the following combinations:

(i) one of X and Y is $CO_2R^y$ and the other is $CH_2CO_2R^x$;

(ii) X is $CHR^6R^7$ and Y is $C(=O)R^9$;

(iii) X is $CR^7=PR^z{}_3$ and Y is $C(=O)R^9$;

(iv) X is $C(=O)R^7$ and Y is $CR^9=PR^z{}_3$;

(v) one of Y and X is COW and the other is $NHR^{11'}$ or $NR11'COW$;

(vi) X is $NHR^{11'}$ and Y is $C(=O)R^8$ or X is $C(=O)R^6$ and Y is $NHR^{11'}$;

(vii) X is $NHR^{11'}$ and Y is $CR^8R^9W$;

(viii) X is W or OH and Y is $CH_2OH$;

(ix) X is $NHR^{11'}$ and Y is $SO_2W$;

(x) one of X and Y is $(CH_2)_p$-W and the other is $(CH_2)_q NHR^{11'}$, $(CH_2)_q OH$, $(CH_2)_q SH$ or $(CH_2)_q SCOR^x$ where p+q=1;

(xi) one of X and Y is OH and the other is —CH=$N_2$;

(xii) X is NCO and Y is OH or $NH_2$;

(xiii) X is $CR^6R^7SO_2W$, A'COW, $CR^6=CH_2$ or oxirane and Y is $NHR^{11'}$;

(xiv) X is W and Y is $CONHR^{11}$ or $OCONH_2$;

in which W is a leaving group; $R^x$ and $R^y$ are $(C_{1-6})$alkyl; $R^z$ is aryl or $(C_{1-6})$alkyl; A' and $NR^{11'}$ are A and $NR^{11}$ as defined in formula (I), and oxirane is:

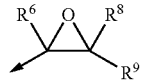

wherein $R^6$, $R^8$ and $R^9$ are as defined in formula (I);

and thereafter optionally or as necessary converting $Z^{1'}$, $Z^{2'}$, $Z^{3'}$, $Z^{4'}$, $Z^{5'}$, $R^{1'}$, $R^{3'}$ and $R^{4'}$ to $Z^1$, $Z^2$, $Z^3$, $Z^4$, $Z^5$, $R^1$, $R^3$ and $R^4$; converting A-B to other A-B, interconverting $R^1$, $R^3$ and/or $R^4$, and/or forming a pharmaceutically acceptable salt, solvate and/or N-oxide thereof.

* * * * *